United States Patent
Tomalia et al.

(10) Patent No.: US 6,177,414 B1
(45) Date of Patent: Jan. 23, 2001

(54) STARBURST CONJUGATES

(75) Inventors: Donald A. Tomalia, Midland; William J. Kruper, Sanford; Roberta C. Cheng, Midland; Ian A. Tomlinson, Midland; Michael J. Fazio, Midland; David M. Hedstrand, Midland; Larry R. Wilson, Beaverton, all of MI (US); Donald A. Kaplan, Cincinnati, OH (US)

(73) Assignee: The Dow Chemical Company, Midland, MI (US)

( * ) Notice: Under 35 U.S.C. 154(b), the term of this patent shall be extended for 0 days.

(21) Appl. No.: 09/521,409

(22) Filed: Mar. 8, 2000

Related U.S. Application Data

(63) Continuation of application No. 08/711,571, filed on Sep. 10, 1996, now abandoned, which is a continuation of application No. 08/036,644, filed on Mar. 24, 1993, which is a continuation of application No. 07/654,851, filed on Feb. 13, 1991, now Pat. No. 5,338,532, which is a continuation-in-part of application No. 07/386,049, filed on Jul. 26, 1989, which is a continuation-in-part of application No. 07/087,266, filed on Aug. 18, 1987, now abandoned, which is a continuation-in-part of application No. 06/897,455, filed on Aug. 18, 1986, now abandoned.

(51) Int. Cl.[7] .................................................. A61K 31/60
(52) U.S. Cl. .................... 514/159; 514/165; 514/166; 521/25; 523/1; 424/78.17
(58) Field of Search ............................ 424/78.17–78.18, 424/78.36, 78.27, 78.31, 484, 486, 501; 514/159, 162–166, 722, 772.1, 772.3, 772.6, 788; 523/1; 521/25, 28, 29; 528/328, 332, 363

(56) References Cited

U.S. PATENT DOCUMENTS

| | | | |
|---|---|---|---|
| 3,200,106 | 8/1965 | Dickson et al. | 260/97.5 |
| 3,445,441 | 5/1969 | Rushton | 260/89.5 |
| 3,514,250 | 5/1970 | Rushton | 21/2.5 |
| 3,528,928 | 9/1970 | Rushton | 252/341 |
| 3,578,643 | 5/1971 | Wood et al. | 260/78.4 |
| 3,580,891 | 5/1971 | Rainer | 260/72 |
| 3,773,739 | 11/1973 | Bonvicini et al. | 260/78 |
| 4,036,808 | 7/1977 | Rembaun et al. | 260/42.51 |

(List continued on next page.)

FOREIGN PATENT DOCUMENTS

| | | |
|---|---|---|
| 05/60604 | 7/1987 | (AU) . |
| 01/15771 | 8/1984 | (EP) . |
| 02/06742 | 8/1987 | (NZ) . |
| 84/02705 | 7/1984 | (WO) . |
| 08/40128 | 8/1985 | (ZA) . |

OTHER PUBLICATIONS

Tomalia et al. (January 1985), *Polymer Journal* vol. 17, No.1, 117–132.

Tomalia et al., *Macrocolecules*, vol. 19, No. 9, 2466–2468, 1986.

Manabe et al. (1986), *Biochim. Biophys, Acta*, 883.

Torchilin et al. (1986), *Byull, Eksp, Biol. Med*, (BEBMAE), 102(7), 63–65.

Rowland et al. (Jun 5, 1975), *Nature*, 225, 387–488.

Curtet et al. (1986), *Proceedings Nat'l Acad, of Sci.* (U.S.A.), vol. 83, 4277–4281.

Anderson (1986), *J. Nucl. Med.*, 27 pp. 829–833.

(List continued on next page.)

*Primary Examiner*—Neil S. Levy
(74) *Attorney, Agent, or Firm*—Karen L. Kimble

(57) ABSTRACT

Starburst conjugates which are composed of at least one dendrimer in association with at least one unit of a carried agricultural, pharmaceutical, or other material have been prepared. These conjugates have particularly advantageous properties due to the unique characteristics of the dendrimer.

4 Claims, 11 Drawing Sheets

U.S. PATENT DOCUMENTS

| | | | |
|---|---|---|---|
| 4,102,827 | 7/1978 | Rembaun et al. | 260/823 |
| 4,141,847 | 2/1979 | Kivosky | 252/51.5 |
| 4,289,872 | 9/1981 | Denkewalter et al. | 528/328 |
| 4,315,087 | 2/1982 | Redmore et al. | 525/421 |
| 4,435,548 | 3/1984 | Tomalia et al. | 525/451 |
| 4,472,509 | 9/1984 | Ganson et al. | 436/548 |
| 4,507,466 | 3/1985 | Tomalia et al. | 528/332 |
| 4,558,120 | 12/1985 | Tomalia et all. | 528/363 |
| 4,568,737 | 2/1986 | Tomalia et al. | 528/332 |
| 4,587,329 | 5/1986 | Tomalia et al. | 528/363 |
| 4,606,907 | 8/1986 | Simon et al. | 424/1.1 |
| 4,631,337 | 12/1986 | Tomalia et al . | 528/391 |
| 4,634,586 | 1/1987 | Goodwin et al. | 424/1.1 |
| 4,675,173 | 6/1987 | Widdor | 424/9 |
| 4,824,659 | 4/1989 | Hawthorne | 424/1.1 |
| 4,871,779 | 10/1989 | Killat et al. | 521/28 |
| 4,916,246 | 4/1990 | Feldre et al. | 556/1 |
| 4,980,148 | 12/1990 | Dean | 424/9 |
| 5,021,236 | 6/1991 | Gries | 424/9 |
| 5,039,512 | 8/1991 | Kraft | 424/9 |

OTHER PUBLICATIONS

Tam (1988), *Proc. Nat'l Acad. Sci.* (U.S.A.), 85, pp. 5409–5413.

Savinova (1985), *Journal Of Molecular Catalysis*, 32, 149–158.

Savinova (1985), *Journal of Molecular Catalysis*, 32, 159–175.

Roberts (1990), *Bioconjugate Chemistry*, 1 305–308.

Tomalia (1990), *Angew Chem., Int. Ed. Engl.*, 29, 138–175.

Generation of added PAMAM Starburst Dendrimer

STARBURST CONJUGATES

CROSS REFERENCE TO RELATED APPLICATION

This application is a continuation of application Ser. No. 08/711,571 now abandoned filed Sep. 10, 1996, which is a continuation of application Ser. No. 08/036,644 filed Mar. 24, 1993, pending which is a continuation of application Ser. No. 07/654,851, filed Feb. 13, 1991, now issued as U.S. Pat. No. 5,338,532, which is a continuation-in-part of our co-pending application Ser. No. 07/386,049 filed Jul. 26, 1989, which is a continuation-in-part of Ser. No. 087,266, filed Aug. 18, 1987, now abandon, which is a continuation-in-part application of Ser. No. 897,455, filed Aug. 18, 1986, now abandon.

FIELD OF THE INVENTION

The present invention concerns the use of dense star polymers as carriers for agricultural, pharmaceutical, and other materials.

BACKGROUND OF THE INVENTION

In recent years polymers referred to as dense star polymers or starburst polymers have been developed. It has been found that the size, shape and properties of these dense star polymers or starburst polymers can be molecularly tailored to meet specialized end uses. Starburst polymers have significant advantages which can provide a means for the delivery of high concentrations of carried material per unit of polymer, controlled delivery, targeted delivery and/or multiple species delivery or use.

SUMMARY OF THE INVENTION

In its broadest aspect, the present invention is directed to polymer conjugate materials comprising dense star polymers or starburst polymers associated with desired materials (hereinafter these polymer conjugates will frequently be referred to as "starburst conjugates" or "conjugates"), process for preparing these conjugates, compositions containing the conjugates, and methods of using the conjugates and compositions.

The conjugates of the present invention are suitable for use in a variety of applications where specific delivery is desired, and are particularly suited for the delivery of biologically active agents. In a preferred embodiment of the present invention, the starburst conjugates are comprised of one or more starburst polymers associated with one or more bioactive agents.

The starburst conjugates offer significant benefits over other carriers known in the art due to the advantageous properties of the starburst polymers. Starburst polymers exhibit molecular architecture characterized by regular dendritic branching with radial symmetry. These radially symmetrical molecules are referred to as possessing "starburst topology". These polymers are made in a manner which can provide concentric dendritic tiers around an initiator core. The starburst topology is achieved by the ordered assembly of organic repeating units in concentric, dendritic tiers around an initiator core; this is accomplished by introducing multiplicity and self-replication (within each tier) in a geometrically progressive fashion through a number of molecular generations. The resulting highly functionalized molecules have been termed "dendrimers" in deference to their branched (tree-like) structure as well as their oligomeric nature. Thus, the terms starburst oligomer and starburst dendrimer are encompassed within the term starburst polymer. Topological polymers, with size and shape controlled domains, are dendrimers that are covalently bridged through their reactive terminal groups, which are referred to as starburst "bridged dendrimers." The term bridged dendrimer is also encompassed within the term "starburst polymer".

BRIEF DESCRIPTION OF THE DRAWINGS

The following description of the figures aid in understanding the present invention.

Example 8 shows the comparison of percent salicylic acid released into the receptor compartment in the presence of starburst polymer (Gen=4.0) at pH 5.0 and 6.65 with salicyclic acid control, Example 4.

Figure 9:
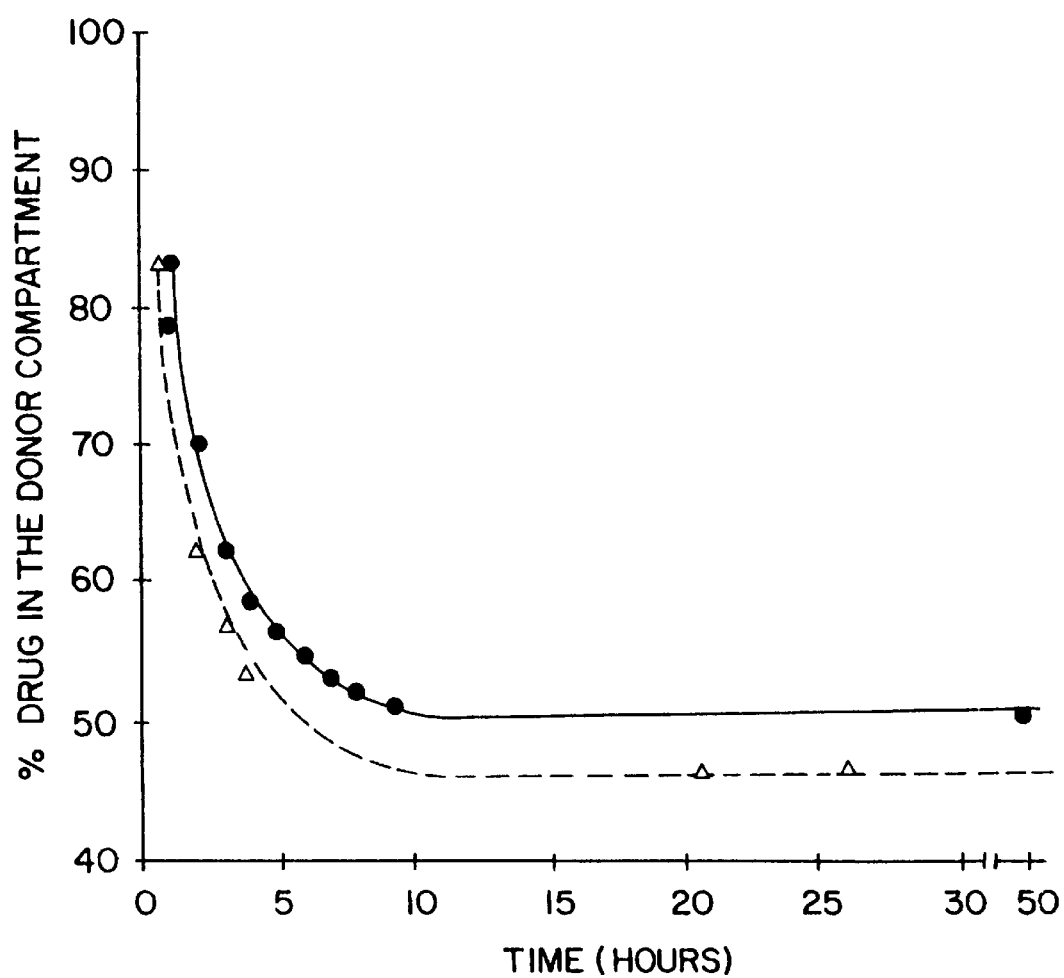

FIG. 9 shows the comparison of percent salicyclic acid lost from donor compartment with starburst polymer (Gen=4.0) in receptor compartment at pH 8.0 to salicyclic acid content, Example 4.

Figure 10:
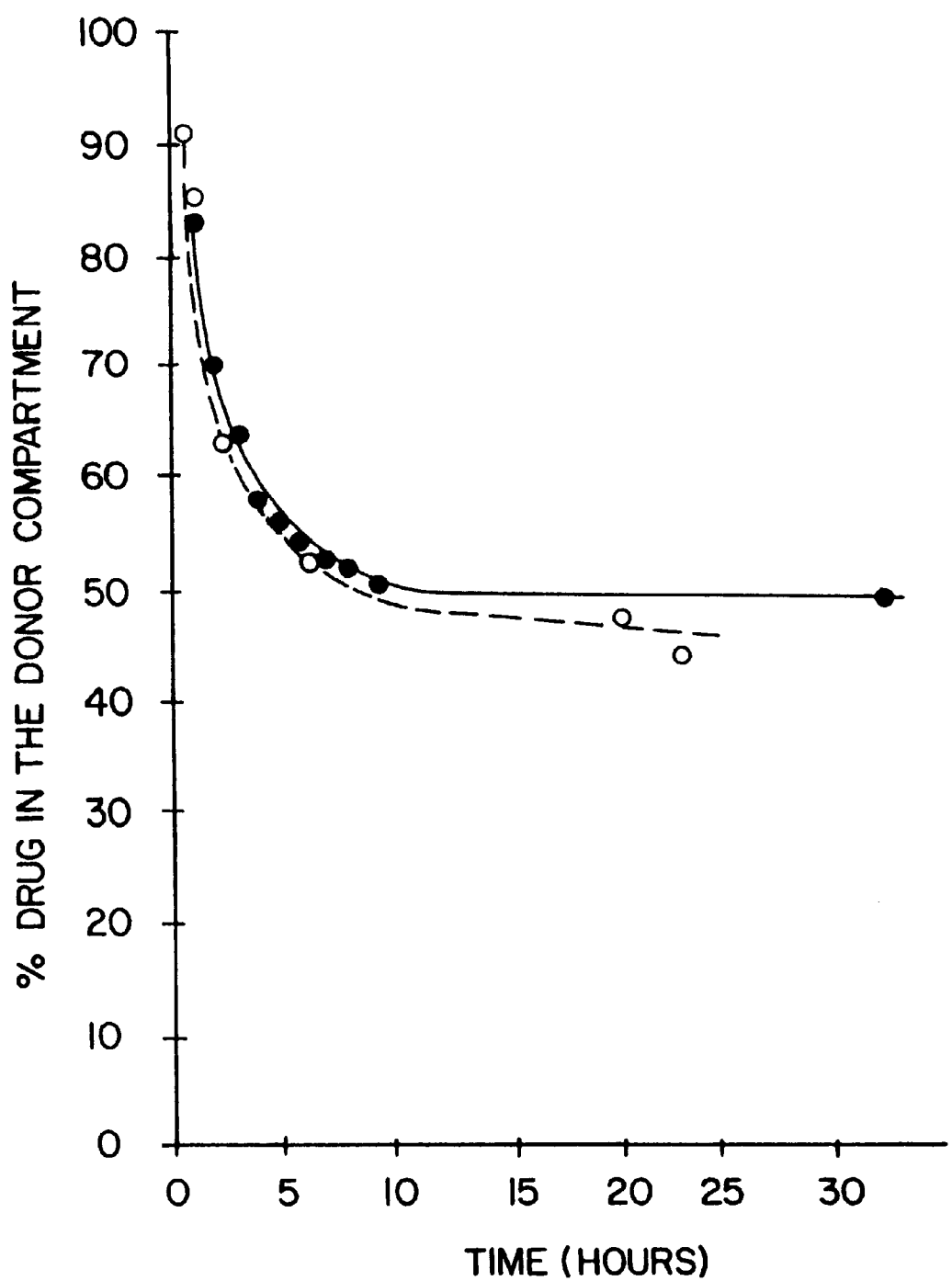

FIG. 10 shows the comparison of percent salicyclic acid lost from donor compartment in presence of starburst polymer (Gen=4.5) to salicyclic acid control, Example 4.

Figure 11:
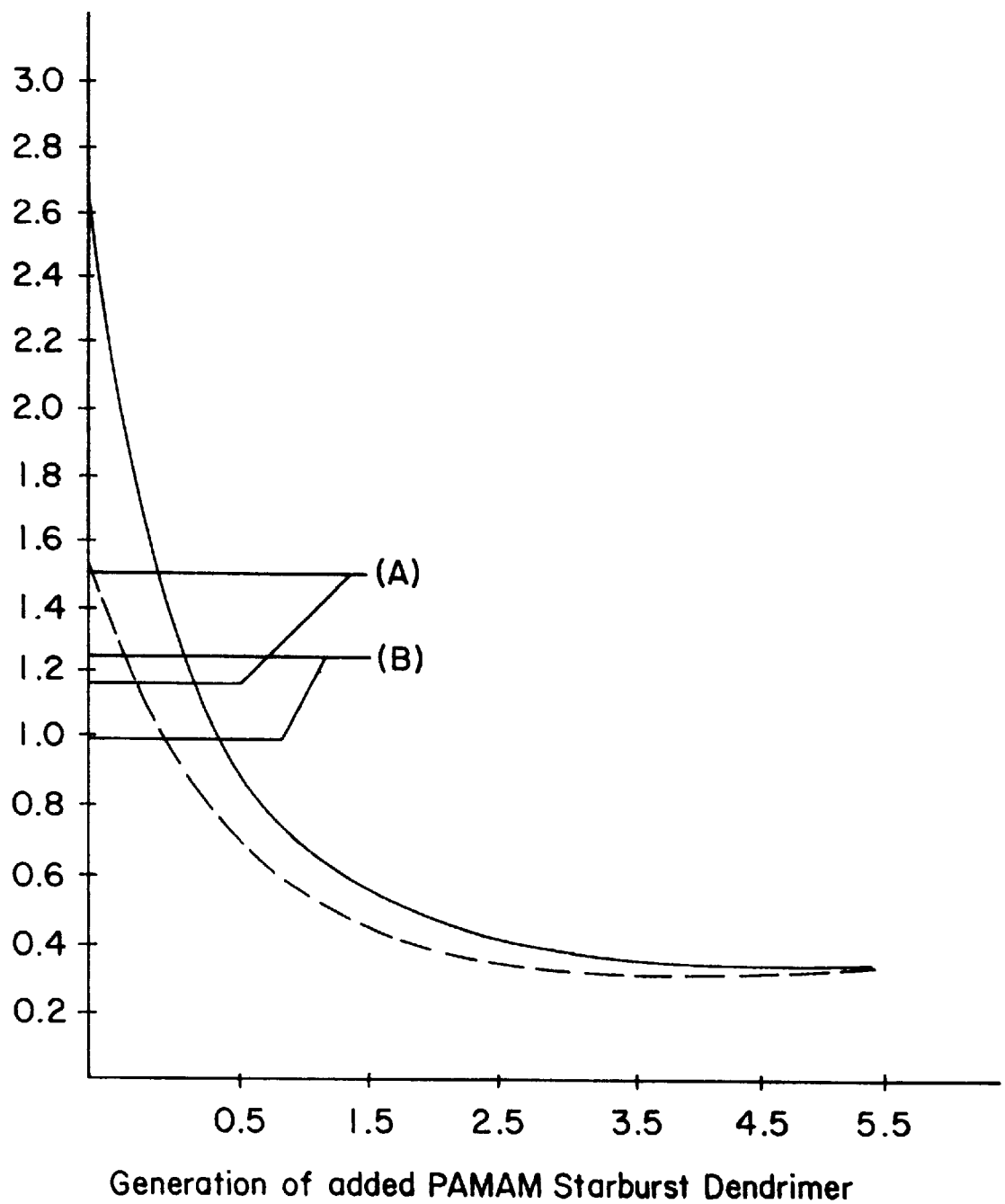

FIG. 11 shows carbon-13 spin lattice relaxation times ($T_1$) for 2,4-D incorporated into various dendrimer generations, Example 14.

Figure 1:
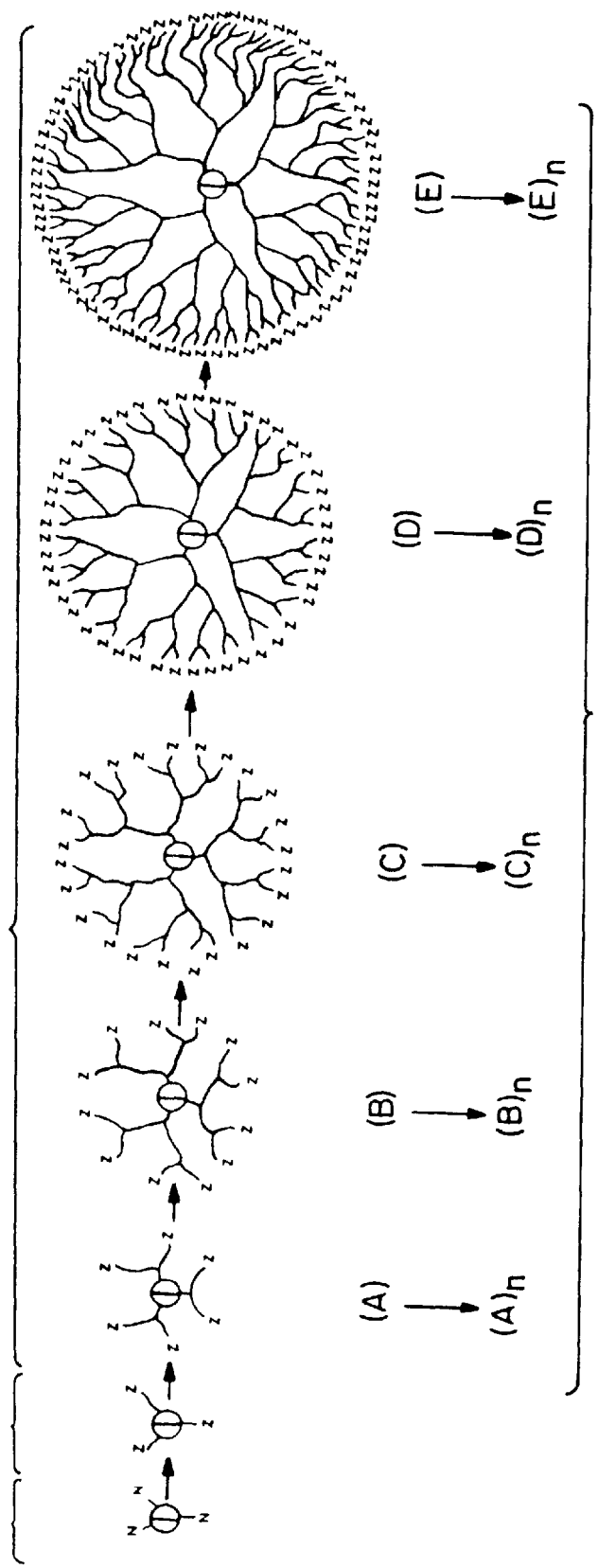
FIG. 1 depicts various generations of starburst dendrimers.

The starburst polymers are illustrated by FIG. 1 wherein (I) represents an initiator core (in this figure a tri-functional initiator core shown by the far left drawing,); Z represents a terminal group, shown in the first instance by the second drawing from the left, referred to as a starbranched oligomer; A, B, C, D, and E represent particular molecular generations of starburst dendrimers; and $(A)_n$, $(B)_n$, $(C)_n$, $(D)_n$, and $(E)_n$ represent starburst bridged dendrimers.

The starburst dendrimers are unimolecular assemblages that possess three distinguishing architectural features, namely, (a) an initiator core, (b) interior layers (generations, G) composed of repeating units, radially attached to the initiator core, and (c) an exterior surface of terminal functionality (i.e., terminal functional groups) attached to the outermost generation. The size and shape of the starburst dendrimer molecule and the functional groups present in the dendrimer molecule can be controlled by the choice of the initiator core, the number of generations (i.e., tiers) employed in creating the dendrimer, and the choice of the repeating units employed at each generation. Since the dendrimers can be isolated at any particular generation, a means is provided for obtaining dendrimers having desired properties.

The choice of the starburst dendrimer components affects the properties of the dendrimers. The initiator core type can affect the dendrimer shape, producing (depending on the choice of initiator core), for example, spheroid-shaped dendrimers, cylindrical or rod-shaped dendrimers, ellipsoid-shaped dendrimers, or mushroom-shaped dendrimers. Sequential building of generations (i.e., generation number and the size and nature of the repeating units) determines the dimensions of the dendrimers and the nature of their interior.

Figure 2:
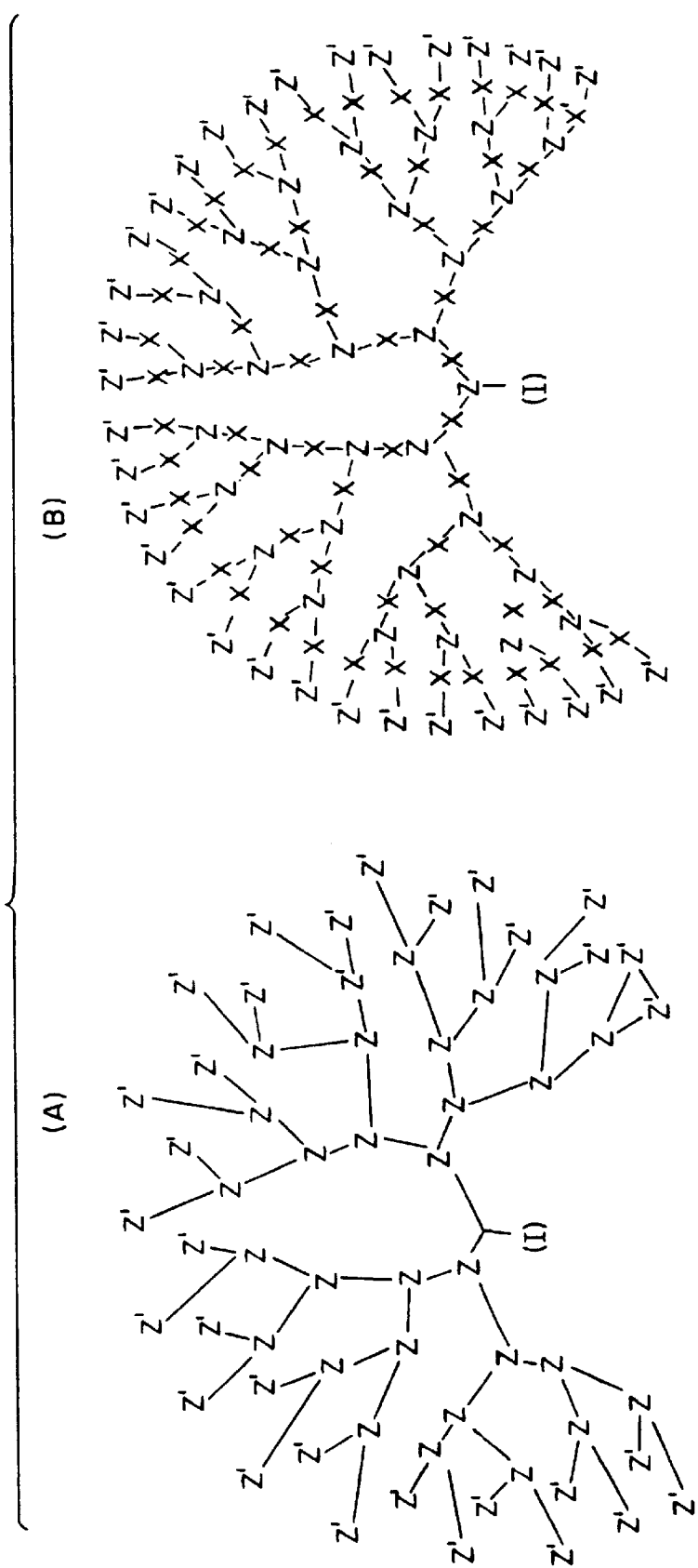
FIG. 2A depicts a dendrimer having unsymmetrical (unequal) branch junctures.
FIG. 2B depicts a dendrimer having symmetrical (equal) branch junctures.

Because starburst dendrimers are branched polymers containing dendritic branches having functional groups distributed on the periphery of the branches, they can be prepared with a variety of properties. For example, the macromolecules depicted in FIG. 2A (such as Denkewalter, U.S. Pat. No. 4,289,872), and the present starburst dendrimers, such as those depicted in FIG. 2B can have distinct properties due to the branch length. The dendrimer type shown in FIG. 2A possesses unsymmetrical (unequal segment) branch junctures, exterior (i.e., surface) groups (represented by Z'), interior moieties (represented by Z) but much less internal void space. The preferred dendrimer type shown in FIG. 2B possesses symmetrical (equal segment) branch junctures with surface groups (represented by Z'), two different interior moieties (represented respectively by X and Z) with interior void space which varies as a function of the generation (G). The dendrimers such as those depicted in FIG. 2B can be advanced through enough generations to totally enclose and contain void space, to give an entity with a predominantly hollow interior and a highly congested surface.

Also, starburst dendrimers, when advanced through sufficient generations exhibit "starburst dense packing" where the surface of the dendrimer contains sufficient terminal moieties such that the dendrimer surface becomes congested and encloses void spaces within the interior of the dendrimer. This congestion can provide a molecular level barrier which can be used to control diffusion of materials into or out of the interior of the dendrimer.

Surface chemistry of the dendrimers can be controlled in a predetermined fashion by selecting a repeating unit which contains the desired chemical functionality or by chemically modifying all or a portion of the surface functionalities to create new surface functionalities. These surfaces may either be targeted toward specific sites or made to resist uptake by particular organs or cells e.g. by reticuloendothelial cells.

In an alternative use of the starburst dendrimers, the dendrimers can themselves be linked together to create polydendric moieties (starburst "bridged dendrimers") which are also suitable as carriers.

In addition, the dendrimers can be prepared so as to have deviations from uniform branching in particular generations, thus providing a means of adding discontinuities (i.e., deviations from uniform branching at particular locations within the dendrimer) and different properties to the dendrimer.

The starburst polymers employed in the starburst conjugates of the present invention can be prepared according to methods known in the art, for example, U. S. Pat. No. 4,587,329, the disclosure of which is hereby incorporated by reference. Polyamine dendrimers may be prepared by reacting ammonia or an amine having a plurality of primary amine groups with N-substituted aziridine, such as N-tosyl or N-mesyl aziridine, to form a protected first generation polysulfonamide. The first generation polysulfonamide is then activated with acid, such as sulfuric, hydrochloric, trifluoroacetic, fluorosulfonic or chlorosulfonic acid, to form the first generation polyamine salt. Preferably, the desulfonylation is carried out using a strong acid which is volatile enough to allow removal by distillation, such as hydrochloric acid. The first generation polyamine salt can then be reacted further with N-protected aziridine to form the protected second generation polysulfonamide. The sequence can be repeated to produce higher generation polyamines.

Polyamidoamines can be prepared by first reacting ammonia with methyl acrylate under conditions sufficient to cause the Michael addition of one molecule of the ammonia to three molecules of the methyl acrylate to form the core adduct. Following removal of unreacted methylacrylate, this compound is reacted with excess ethylenediamine under conditions such that one amine group of the ethylenediamine molecule reacts with the methyl carboxylate groups of the core adduct to form a first generation adduct having three amidoamine moieties. Following removal of unreacted ethylenediamine, this first generation adduct is then reacted with excess methyl acrylate under Michael's addition conditions to form a second generation adduct having terminal methyl ester moieties. The second generation adduct is then reacted with excess ethylenediamine under amide forming conditions to produce the desired polyamidoamine dendrimer having ordered, second generation dendritic branches with terminal amine moieties. Similar dendrimers containing amidoamine moieties can be made by using organic amines as the core compound, e.g., ethylenediamine which produces a tetra-branched dendrimer or diethylenetriamine which produces a penta-branched dendrimer.

To prepare anhydrous starburst polyethylenimines, after acid cleavage of the sulfonamide bonds, a solvent which will form an azeotrope with water, such as benzene, toluene, xylene or mesitylene, preferably toluene, can be added and the resulting water/solvent azeotrope removed by azeotropic distillation, such as by heating the mixture to reflux with water removal carried out by a Dean-Stark trap. Alternatively, chlorinated solvents in which anhydrous polyethylenimine is soluble, such as chloroform, can be used in the drying step. The addition of a chlorinated solvent or solvent which forms an azeotrope with water, avoids the necessity of having to heat the polymer at temperatures which char or degrade the polymer. Anhydrous polyethylenimines are particulary useful as carriers for antigenic materials.

Dendrimers can be prepared having highly uniform size and shape and most importantly allow for a greater number of functional groups per unit of surface area of the dendrimer, and can have a greater number of functional groups per unit of molecular volume as compared to other polymers which have the same molecular weight, same core and monomeric components and same number of core branches as the starburst polymers. The increased functional group density of the dense starburst polymers may allow a greater quantity of material to be carried per dendrimer. Since the number of functional groups on the dendrimers can be controlled on the surface and within the interior, it also provides a means for controlling, for example, the amount of bioactive agent to be delivered per dendrimer. In a particularly preferred embodiment of the present invention, the starburst polymers, particularly the starburst dendrimers, are targeted carriers of bioactive agents capable of delivering the bioactive agents to a particular target organism or to a particular determinant or locus in a target organism.

An analogy can be made between early generation starburst dendrimers (i.e. generation=1–7) and classical spherical micelles. The dendrimer-micelles analogy was derived by comparing features which they had in common such as shape, size and surface.

TABLE I

| Parameter | Regular classical Micelles | Starburst Dendrimers |
|---|---|---|
| Shape | Spherical | Spherical |
| Size (diameter) | 20–60Å | 17–67Å |
| Surface aggregation number | 4–202 | Z = 6–192 (Z is the number of surface groups) (generation = 2–7) |
| area/surface group (Å$^2$) | 130–80Å$^2$ | 127–75Å$^2$ |

(1Å = 10$^{-1}$nm; 1Å$^2$ = 10$^{-2}$nm$^2$

Table I, the shape was verified by scanning transmission electron micrographs (STEM) microscopy and intrinsic viscosity ($\eta$) measurements. The size was verified by intrinsic viscosity [$\eta$] and size exclusion chromatography (SEC) measurements. The surface aggregation numbers were verified by titrimetry and high field NMR. The area/surface group was calculated from SEC hydrodynamic measurements.

The first five generations of starburst polyamidoamine (PAMAM) dendrimers are microdomains which very closely mimic classical spherical micelles in nearly every respect (i.e., shape, size, number of surface groups, and area/surface groups). A major difference, however, is that they are covalently fixed and robust compared to the dynamic equilibrating nature of micelles. This difference is a significant advantage when using these microdomains as encapsulation devices.

As further concentric generations are added beyond five, congestion of the surface occurs. This congestion can lead to increased barrier characteristics at the surface and manifests itself as a smaller surface area per head (surface) group as shown in Table II.

like surface normally associated with vesicles (liposomes) or Langmuir-Blodgett type membranes.

If this surface congestion is occurring, the change in physical characteristics and morphology should be observed as the generations increase from the intermediate generation (6–8) to the more advanced generations (9 or 10). The scanning transmission electron micrographs (STEM) for generations=7.0, 8.0 and 9.0 were obtained after removing the methanol solvent from each of the samples to provide colorless, light yellow solid films and staining with osmium tetraoxide. The morphological change predicted occurred at the generation G=9.0 stage. The microdomains at generation=9.0 measure about 33 Å in diameter and are surrounded by a colorless rim which is about 25 Å thick. Apparently methanolic solvent has been entrapped within the 25 Å outer membrane-like barrier to provide the dark stained interior. Thus, at generation=9.0, the starburst PAMAM is behaving topologically like a vesicle (liposome). However, this starburst is an order of magnitude smaller and very monodispersed compared to a liposome and is much more physically stable than a liposome. Consequently, the present dendrimers can be used to molecularly encapsulate solvent filled void spaces of as much diameter as about 33 Å (volume about 18,000 Å$^3$) or more. These micelle sized prototypes appear to behave like a covalently fixed liposome in this advanced generation stage. This behavior enables these prototypes to have additional capability as carriers for, for example, non-chelating radionuclides in starburst antibody conjugates for the treatment of various mammalian diseases.

Since the number of functional groups on the dendrimers can be controlled on the surface and within the interior, it also provides a means for controlling the amount of carried material to be delivered per dendrimer. In one embodiment, the dendrimers are targeted carriers of agents capable of delivering the carried material, for example, a bioactive agent, to, for example, a plant or pest or a particular determinant or locus in a target organism.

Dendrimers suitable for use in the conjugates of the present invention include the dense star polymers or star-

TABLE II

PAMAM Dendrimer Features vs. Generation

| Generations | 1 | 2 | 3 | 4 | 5 | 6 | 7 | 8 | 9 |
|---|---|---|---|---|---|---|---|---|---|
| # of surface groups, Z | 3 | 6 | 12 | 24 | 48 | 96 | 192 | 384 | 768 |
| Molecular wt. | 275 | 875 | 2411 | 5147 | 10,619 | 21,563 | 43,541 | 87,227 | 174,779 |
| Diameter* measured SEC | 10.4Å | 15.8Å | 22Å | 31Å | 40Å | 53Å | 67Å | 76Å | 88Å |
| Surface area per dendrimer | 366Å$^2$ | 783Å$^2$ | 1519Å$^2$ | 3018Å$^2$ | 5024Å$^2$ | 8,820Å$^2$ | 14,096Å$^2$ | 18,136Å$^2$ | 36,083Å$^2$ |
| Surface area per Z group | 122Å$^2$ | 131Å$^2$ | 127Å$^2$ | 126Å$^2$ | 104Å$^2$ | 92Å$^2$ | 73Å$^2$ | 47Å$^2$ | 32Å$^2$ |
| Distance between Z groups | 12.4Å | 12.8Å | 12.7Å | 12.6Å | 11.5Å | 10.8Å | 9.8Å | 7.75Å | 6.28Å |
| Void Volume | 311.6Å$^3$ | 1,470.2Å$^3$ | 4,737.9Å$^3$ | 11,427.0Å$^3$ | — | — | — | — | — |

*Hydrodynamic diameters determined by size exclusion chromatogaphy measurements calibrated against monodisperse $\left(\frac{Mw}{Mn} = 1.02\right)$ polyethyleneoxide standards.
1Å = 10$^{-1}$ nm; 1Å$^2$ = 10$^{-2}$ nm$^2$; 1Å$^3$ = 10$^{-3}$ nm$^3$.

For example, amine terminated generations 5.0, 6.0, 7.0, 8.0 and 9.0 have decreased surface areas of 104, 92, 73, 47 and 32 Å$^2$ per Z group, respectively. This characteristic corresponds to a transition from a less congested micelle-like surface to a more congested bi-layer/monolayer barrierburst polymers described in U.S. Pat. Nos. 4,507,466, 4,558, 120, 4,568,737 and 4,587,329.

In particular, the present invention concerns a starburst conjugate which comprises at least one starburst polymer associated with at least one carried agricultural, pharmaceutical, or other material. Starburst conjugates included within the scope of the present invention include those represented by the formula:

$$(P)_x *(M)_y \quad (I)$$

wherein
each P represents a dendrimer;
x represents an integer of 1 or greater;
each M represents a unit (for example, a molecule, atom, ion, and/or other basic unit) of a carried material, said carried material can be the same carried material or a different carried material, preferably the carried material is a bioactive agent;
y represents an integer of 1 or greater; and
* indicates that the carried material is associated with the dendrimer.

Preferred starburst conjugates of formula (I) are those in which M is a drug, pesticide, radionuclide, chelant, chelated metal, toxin, antibody, antibody fragment, antigen, signal generator, for example, fluorescing entities, signal reflector, for example, paramagnetic entities, or signal absorber, for example, electron beam opacifiers, fragrance, pheromones, or dyes. It is particularly preferred that x=1 and y=2 or more.

Also included are starburst conjugates of formula (I) wherein the starburst dendrimers are covalently linked together, starburst bridged dendrimers, optionally via linking groups, so as to form polydendric assemblages (i.e., where x>1). Uses of these starburst bridged dendrimers include topical controlled release agents, radiation synovectomy, and others.

As used herein, "associated with" means that the carried material(s) can be physically encapsulated or entrapped within the core of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Waals forces or ionic bonding, or any combination thereof. The association of the carried material(s) and the dendrimer (s) may optionally employ connectors and/or spacers to facilitate the preparation or use of the starburst conjugates. Suitable connecting groups are groups which link a targeting director (i.e., T) to the dendrimer (i.e., P) without significantly impairing the effectiveness of the director or the effectiveness of any other carried material(s) (i.e., M) present in the starburst conjugate. These connecting groups may be cleavable or non-cleavable and are typically used in order to avoid steric hindrance between the target director and the dendrimer, preferably the connecting groups are stable (i.e., non-cleavable). Since the size, shape and functional group density of the starburst dendrimers can be rigorously controlled, there are many ways in which the carried material can be associated with the dendrimer. For example, (a) there can be covalent, coulombic, hydrophobic, or chelation type association between the carried material(s) and entities, typically functional groups, located at or near the surface of the dendrimer; (b) there can be covalent, coulombic, hydrophobic, or chelation type association-between the carried material(s) and moieties located within the interior of the dendrimer; (c) the dendrimer can be prepared to have an interior which is predominantly hollow allowing for physical entrapment of the carried materials within the interior (void volume), wherein the release of the carried material can optionally be controlled by congesting the surface of the dendrimer with diffusion controlling moieties; or (d) various combinations of the aforementioned phenomena can be employed.

Dendrimers, herein represented by "P", include the dense star polymers described in U.S. Pat. Nos. 4,507,466, 4,558,120, 4,568,737 or 4,587,329.

In a preferred embodiment, the carried materials, herein represented by "M", are pharmaceutical materials. Such materials which are suitable for use in the starburst conjugates include any materials for in vivo or in vitro use for diagnostic or therapeutic treatment of mammals which can be associated with the dense star dendrimer without appreciably disturbing the physical integrity of the dendrimer, for example: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valban; toxins, such as diphtheria toxin, gelonin, exotoxin A, abrin, modeccin, ricin, or toxic fragments thereof; metal ions, such as the alkali and alkaline-earth metals; radionuclides, such as those generated from actinides or lanthanides or other similar transition elements or from other elements, such as $^{47}Sc$, $^{67}Cu$, $^{67}Ga$, $^{82}Rb$, $^{89}Sr$, $^{88}Y$, $^{90}Y$, $^{99m}Tc$, $^{105}Rh$, $^{109}Pd$, $^{111}In$, $^{115m}In$, $^{125}I$, $^{131}I$, $^{140}Ba$, $^{140}La$, $^{149}Pm$, $^{153}Sm$, $^{159}Gd$, $^{166}Ho$, $^{175}Yb$, $^{177}Lu$, $^{186}Re$, $^{188}Re$, $^{194}Ir$, and $^{199}Au$, preferably $^{88}Y$, $^{90}Y$, $^{99m}Tc$, $^{125}I$, 131I, $^{153}Sm$, $^{166}Ho$, $^{177}Lu$, $^{186}Re$, $^{67}Ga$, $^{111}In$, $^{115m}In$, and $^{140}La$; signal generators, which includes anything that results in a detectable and measurable perturbation of the system due to its presence, such as fluorescing entities, phosphoresence entities and radiation; signal reflectors, such as paramagnetic entities, for example, Fe, Gd, or Mn; chelated metal, such as any of the metals given above, whether or not they are radioactive, when associated with a chelant; signal absorbers, such as contrast agents and electron beam opacifiers, for example, Fe, Gd or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Carried pharmaceutical materials include scavenging agents such as chelants, antigens, antibodies or any moieties capable of selectively scavenging therapeutic or diagnostic agents.

In another embodiment, the carried materials, herein represented by "M", are agricultural materials. Such materials which are suitable for use in the starburst conjugates include any materials for in vivo or in vitro treatment, diagnosis, or application to plants or non-mammals (including microorganisms) which can be associated with the starburst dendrimer without appreciably disturbing the physical integrity of the dendrimer. For example, the carried materials can be toxins, such as diphtheria toxin, gelonin, exotoxin A, abrin, modeccin, ricin, or toxic fragments thereof; metal ions, such as the alkali and alkaline earth metals; radionuclides, such as those generated from actinides or lanthanides or other similar transition elements or from other elements, such as $^{47}Sc$, $^{67}Cu$, $^{67}Ga$, $^{82}Rb$, $^{89}Sr$, $^{88}Y$, $^{90}Y$, $^{99m}Tc$, $^{105}Rh$, $^{109}Pd$, $^{111}In$, $^{115}In$, $^{125}I$, $^{131}I$, $^{140}Ba$, $^{140}La$, 149Pm, $^{153}Sm$, $^{159}Gd$, $^{166}Ho$, $^{175}Yb$, $^{177}Lu$, $^{186}Re$, $^{188}Re$, $^{194}Ir$ and $^{199}Au$; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such contrast agents and as electron beam opacifiers, for example, Fe, Gd, or Mn; hormones; biological response modifiers, such as interleukins, interferons, viruses and viral fragments; pesticides, including antimicrobials, algicides, arithelmetics, acaricides, II insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermithrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam, pendimethalin, permethrin, picloram, propachlor, propanil, sethoxydin, temephos, terbufos, trifluralin, triforine, zineb, and the like. Carried agricultural materials include scavenging agents such as chelants, chelated metal (whether or not they are radioactive) or any moieties capable of selectively scavenging therapeutic or diagnostic agents.

In another embodiment, the carried material, herein represented by "M", are immuno-potentiating agents. Such materials which are suitable for use in the starburst conjugates include any antigen, hapten, organic moiety or organic or inorganic compounds which will raise an immuno-response which can be associated with the starburst dendrimers without appreciably disturbing the physical integrity of the dendrimers. For example, the carried materials can be synthethic peptides used for production of vaccines against malaria (U.S. Pat. No. 4,735,799), chollera (U.S. Pat. No. 4,751,064) and urinary tract infections (U.S. Pat. No. 4,740,585), bacterial polysaccarides for producing antibacterial vaccines (U.S. Pat. No. 4,695,624) and viral proteins or viral particles for production of antiviral vaccines for the prevention of diseases such as AIDS and hepatitis.

The use of starburst conjugates as carriers for immuno-potentiating agents avoids the disadvantages of ambiguity in capacity and structure associated with conventionally known or synthetic polymer conjugates used to give a macromolecular structure to the antigen-carrier. Use of the starburst dendrimers as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic petides or groups to the starburst dendrimer, such as attachment of both T- and B-cell epitopes. Such a design would lead to improved vaccines.

It may also be desirable to conjugate pesticides or pollutants capable of eliciting an immune response, such as those containing carbamate, triazine or organophosphate consituents, to a starburst dentrimer. Antibodies produced to the desired pesticide or pollutant can be purified by standard procedures, immobilized on a suitable support and be used for subsequent detection of the pesticide or pollutant in the environment or in an organsim.

In a further embodiment, the carried materials, herein represented by "M", which are suitable for use in the starburst conjugates include any materials other than agricultural or pharmaceutical materials which can be associated with the starburst dendrimer without appreciably disturbing the physical integrity of the dendrimer, for example: metal ions, such as the alkali and alkaline-earth metals; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such as contrast agents and an electron beam opacifiers, for example, Fe, Gd, or Mn; pheromone moieties; fragrance moieties; dye moieties; and the like. Carried materials include scavenging agents such as chelants or any moieties capable of selectively scavenging a variety of agents.

Preferably the carried materials are bioactive agents. As used herein, "bioactive" refers to an active entity such as a molecule, atom, ion and/or other entity which is capable of detecting, identifying, inhibiting, treating, catalyzing, controlling, killing, enhancing or modifying a targeted entity such as a protein, glycoprotein, lipoprotein, lipid, a targeted cell, a targeted organ, a targeted organism [for example, a microorganism, plant or animal (including mammals such as humans)] or other targeted moiety.

The starburst conjugates of formula (I) are prepared by reacting P with M, usually in a suitable solvent, at a temperature which facilitates the association of the carried material (M) with the starburst dendrimer (P).

Suitable solvents are solvents in which P and M are at least partially miscible and inert to the formation of the conjugate. If P and M are at least partially miscible with each other, no solvent may be required. When desired, mixtures of suitable solvents can be utilized. Examples of such suitable solvents are water, methanol, ethanol, chloroform, acetonitrile, toluene, dimethylsulfoxide and dimethylformamide.

The reaction conditions for the formation of the starburst conjugate of formula (I) depend upon the particular dendrimer (P), the carried material (M), and the nature of the bond (*) formed. For example, if P is the PEI (polyethyleneimine) starburst dendrimer with a methylene carboxylate surface, M is a radionuclide, e.g. yttrium, then the reaction is conducted at room temperature in water. However, if P is an ester terminated polyamidoamide (PAMAM) starburst dendrimer, M is aspirin, then the reaction is conducted at room temperature in chloroform. Typically, the temperature can range from room temperature to reflux. The selection of the particular solvent and temperature will be apparent to one skilled in the art.

The ratio of M:P will depend on the size of the dendrimer and the amount of carried material. For example, the molar ratio (ratio of moles) of any ionic M to P usually is 0.1–1,000:1, preferably 1–50:1, and more preferably 2–6:1. The weight ratio of any drug, pesticide, organic or toxin M to P usually is 0.1–5:1, and preferably 0.5–3:1.

When M is a radionuclide, there are three ways the starburst conjugate can be prepared, namely: (1) P can be used as a chelant. For example, a methylene-carboxylate surface PEI or PAMAM will chelate a metal such as yttrium or indium. (2) A chelate can be covalently bonded to P. For example, an amine terminated PEI starburst dendrimer can be reacted with 1-(p-isothiocyanatobenzyl) diethylenetriaminepenta-acetic acid and then chelated, or a complex such as rhodium chloride chelated with isothiocyanatobenzyl-2,3,2-tet can be reacted. (3) A prechelated radionuclide can be associated with P by hydrophobic or ionic interaction.

Other starburst conjugates, which are particularly preferred for use with pharmaceutical materials, are those conjugates which contain a target director (herein designated as "T") and which are represented by the formula:

$$(T)_e{}^*(P)_x{}^*(M)_y \qquad (II)$$

wherein
each T represents a target director;

e represents an integer of 1 or greater; and

P, x, *, M, and y are as previously defined herein.

Preferred among the starburst conjugates of formula (II) are those in which M is a drug, pesticide, radionuclide, chelator, chelated metal, toxin, signal generator, signal reflector, or signal absorber. Also preferred conjugates are those conjugates in which e=1 or 2; and those in which x=1 and y=2 or more. Particularly preferred conjugates are those in which x=1, e=1, y=2 or more and M and T are associated with the polymer via the same or different connectors.

The starburst conjugates of formula (II) are prepared either by forming T*P and then adding M or by forming P*M and then adding T. Either reaction scheme is conducted at temperatures which are not detrimental to the particular conjugate component and in the presence of a suitable solvent when required. To control pH, buffers or addition of suitable acid or base is used. The reaction conditions are dependent on the type of association formed (*), the starburst dendrimer used (P), the carried material (M), and the target director (T). For example, when T is a monoclonal antibody and M is a radionuclide, the T*P association is done through a functional group such as an isothiocyanate in water or in water with an organic modifier such as acetonitrile or dimethylformamide. Usually, the conjugation is done in a buffer at pH 7–10, preferably pH 8.5–9.5. The formed conjugate is then chelated with a radionuclide such as yttrium acetate, preferably at room temperature. Alternatively, P and M can be chelated, usually in water, before conjugation to T. The conjugation with T is carried out in a suitable buffer.

The ratio of T:P is preferably 1:1, especially when T is an antibody or fragment. The ratio of M:P will be as before.

Target directors capable of targeting the starburst conjugates are entities which when used in the starburst conjugates of the present invention result in at least a portion of the starburst conjugates being delivered to a desired target (for example, a protein, glycoprotein, lipoprotein, lipid, a targeted cell, a targeted organ, a targeted organism or other targeted moiety) and include antibodies, preferably monoclonal antibodies, antibody fragments such as Fab, Fab', F(ab')$_2$ fragments or any other antibody fragments having the requisite target specificity, hormones, biological response modifiers; epitopes; chemical functionalities exhibiting target specificity; and the like.

The antibodies or antibody fragments which may be used in preferred starburst conjugates described herein can be prepared by techniques well known in the art. Highly specific monoclonal antibodies can be produced by hybridization techniques well known in the art, see, for example, Kohler and Milstein (1975, *Nature* 256:495–497; and 1976, *Eur. J. Immunol.* 6:511–519). Such antibodies normally have a highly specific reactivity.

In the antibody targeted starburst conjugates, antibodies directed against any antigen or hapten may be used. Although conventional polyclonal antibodies may be used, monoclonal antibodies offer several advantages. Each monoclonal antibody is highly specific for a single epitope. In addition, large amounts of each monoclonal antibody can be produced. Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. For a more complete list of antigens see U.S. Pat. No. 4,193,983.

It may be desirable to connect more antibodies or fragments to the dendrimer, and in particular instances to connect antibodies of different specificities. For example, a bifunctional conjugate which has the ability to localize and bind to a tumor and then scavenge circulating cytotoxic, diagnostic, or biostatic compounds can be designed.

In the absence of a target director (or in the presence of a target director if desired), due to the number of functional groups which can be located at or near the surface of the dendrimer, all or a substantial portion of such functional groups can be made anionic, cationic, hydrophobic or hydrophilic to effectively aid delivery of the starburst conjugate to a desired target of the opposite charge or to a hydrophobic or hydrophilic compatible target.

Preparation of the conjugates of formula (II) using a P with a protected handle (S) is also intended as a process to prepare the conjugates of formula (II). The reaction scheme is shown below:

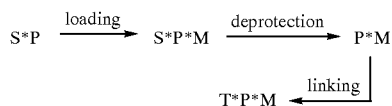

where
S*P represents the protected dendrimer;
S*P*M represents the protected dendrimer conjugated with M;
P*M represents the dendrimer conjugated with M (starburst conjugate);
T*P*M represents the starburst conjugate linked to the target director.

Suitable solvents can be employed which do not effect P*M. For example when S is t-butyloxycarbonyl, S can be removed by aqueous acid.

Also preferred when the carried materials are pharmaceutical materials are starburst conjugates in which the polymer is associated directly, or via connectors; these starburst conjugates are represented by the formula:

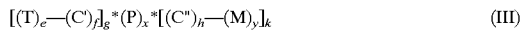

wherein
each C' represents the same or different connecting group;
each C" represents the same or different connecting group;
g and k each individually represent an integer of 1 or greater;
f and h each individually represent an integer of 0 or greater;
— indicates a covalent bond in instances where a connecting group is present; and
P, x, *, M, y, T, and e are as previously defined herein.

Preferred among the starburst conjugates of formula (III) are those in which M is a radionuclide, drug, toxin, signal generator, signal reflector or signal absorber. Also preferred are those conjugates in which x=1. Particularly preferred conjugates are those in which x, e, f, h, and y are each 1, and g is 1 or more and k is 2 or more. Most preferred are those conjugates in which x, e, f, h, y and g are each 1, and k is 2 or more. Also particularly preferred are those starburst conjugates in which M represents a bioactive agent such as a radionuclide, drug, or toxin.

Suitable connecting groups which are represented by C" are groups which link the carried pharmaceutical material to the dendrimer without significantly impairing the effectiveness of the carried pharmaceutical material or the effectiveness of the target director(s) present in the starburst conjugate. These connectors must be stable (i.e., non-cleavable) or cleavable depending upon the mode of activity of the carried pharmaceutical material and are typically used in order to avoid steric hindrance between the carried pharmaceutical material and the polymer.

Most preferred are conjugates in which the dendrimer is associated directly, or via connecting group(s), to one antibody or antibody fragment. The polymer in these preferred conjugates may, in addition, be optionally associated either directly, or via connecting group(s), to one or more other carried materials, preferably a radioisotope. Such starburst conjugates are represented by the formula:

$$[(Antibody)_e\text{---}(C')_f]_g *(P)_x*[(C'')_h\text{---}(M)_y]_k \qquad (IV)$$

wherein each Antibody represents an antibody or antibody fragment capable of interacting with a desired epitope;
— indicates a covalent or coulombic bond in instances where a connecting group is present; and
P, x, *, M, T, e, y, C', C'', g, k, f, and h are as previously defined herein.

For the above synthesis of starburst dendrimers (P) which have a functional group available for linking (C' or C'') with a targeting director (T), the preferred process requires that the reactive functionality be protected as a synthetic precursor. This protection is preferred because it enables the synthesis of dendrimer or conjugates of very high quality. This process allows for the chemical binding of a unit of carried pharmaceutical material (M) to the terminal functional groups of the starburst dendrimer (P) in ways which would otherwise result also in reaction with a linking functional group, thus making it impossible to attach to the targeting director (T). Subsequent deprotection or synthetic conversion into the desired linking functional group thus enables the starburst conjugate to be linked to the targeting director.

One of the preferred "functional groups for linking" (hereafter referred to as a "handle") is an aniline moiety. This group is preferred because it can be used directly for linking to the targeting director, or it can be readily modified to other functional groups suitable for reaction with the targeting director, e.g. isothiocyanate, isocyanate, semithiocarbazide, semicarbazide, bromoacetamide, iodoacetamide, and maleimide. The aniline moiety is also preferred as a handle for linking with the targeting directors because it can be readily protected for use in starburst dendrimer synthesis, or the nitro group can be used as a precursor which can be converted into the desired amino function at the end of the synthesis.

There are a number of protecting groups which are suitable for protecting the anilino amino functionality during starburst dendrimer synthesis. (See Theodora W. Green, *Protective Groups In Organic Synthesis.,* Pub. John Wiley & Son, New York, 1981). A preferred class of protecting groups are the carbamates shown below, wherein R' represents a dendrimer.

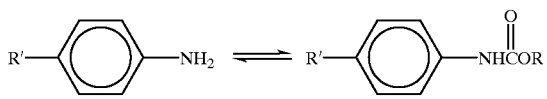

Many carbamates have been used for protection of amines. The most preferred carbamates for starburst dendrimer synthesis is the t-butoxycarbamate, R=—C(CH$_3$)$_3$. Deprotection is achieved by mild acid hydrolysis. Also preferred is the benzylcarbamate protecting group,

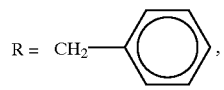

which is preferred when the dendrimer is susceptible to acid hydrolysis. Deprotection is achieved by catalytic hydrogenation.

Other protecting groups which can be used for protecting the reactive moieties at the desired generation level include 9-fluorenylmethylcarbamate

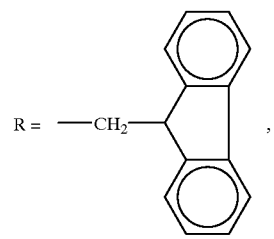

and the phthalimide protecting group,

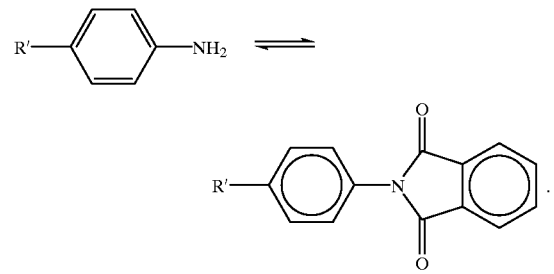

Other protecting groups used for amines which are well known in the literature could also be used in this synthetic scheme. The above preferences are given as illustrative examples only but are not the only protecting groups which can be used. Any protecting group which is stable under the reaction conditions and can be removed without altering the integrity of the starburst dendrimer can be employed.

An alternate process involves the reaction of an activated aryl halide, e.g. 4-nitrofluorobenzene, 2,4-dinitrofluorobenzene, with an amino-function; on the agent for conjugation, e.g. starburst polyethyleneimines (PEI), and subsequent catalytic hydrogenation of the nitro group to the aniline functionality for subsequent conjugation. It is particularly useful for agents, e.g. polyamines, which need further modification prior to use, due to the relative chemical inertness of the nitrophenyl functionality to all non-reducing reaction conditions. The more common bifunctional linking agents, e.g. active esters or diisocyanates, which are reactive under a large number of reaction conditions and which would render them usable for conjugation, include:

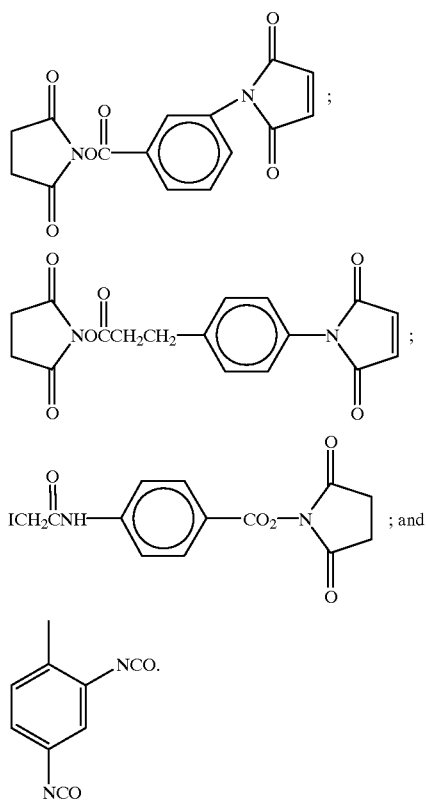

The invention also includes the use of nitro-substituted arylsulphonyl halides to give sulphonamides,

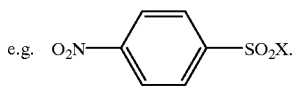

The advantage of this process over known processes of introducing an aminophenyl group for conjugation is that it takes place at a late stage of the synthesis. Gansow et al., U.S. Pat. No. 4,472,509, in his process introduced the nitrophenyl group at the first step of a long synthetic procedure, thereby having limitations on the chemistry available.

This process also introduces a handle which is clearly differentiable from the remainder of the molecule. Manabe et al., disclosed that the ring opening of succinic anhydride by residual amines gave a coupling group through which conjugation to an antibody was possible. This method however gave no means of differentiating between any unchelated sites on the polymer, since the chelating groups were the same as the linking group.

The above process can introduce an aminophenyl functionality into any agent containing an amino group which is then conjugated with some bioactive agent, e.g. monoclonal antibody or enzyme. The agent can be conjugated by oxidative coupling to carbohydrates on the bioactive agent, e.g. antibody. The aminophenyl group also can be converted into an isothiocyanate or isocyanate for subsequent reaction with the pendant amino groups of lysine residues on the bioactive agent.

The present process also provides for direct chelation of lanthanides with starburst dendrimers, preferably by PEI acetate dendrimer. In contrast, Denkewalter, U.S. Pat. No. 4,289,872, states that just putting acetates on the surface works. However, the present reaction shows that PEI acetate, works much better than PAMAM, i.e., surface of iminodiacetates is only part of the story, the nature of the backbone, and branching is very important as well. The PEI acetate has better chelating properties than the PAMAM acetate.

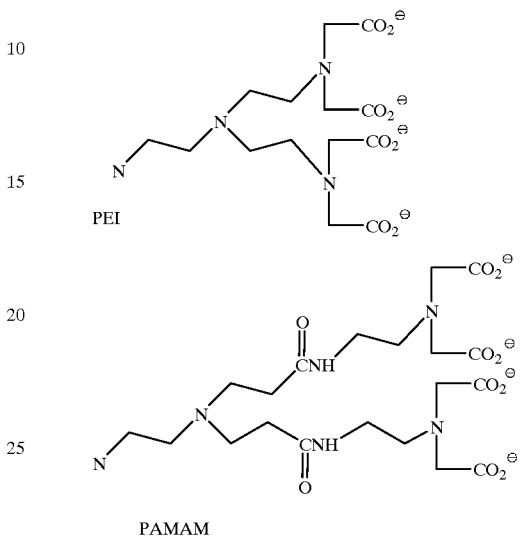

Preferred among the starburst conjugates of formula (IV) are those in which M is a radionuclide, drug, toxin, signal generator, signal reflector or signal absorber. Also preferred are those conjugates in which x=1. Particularly preferred are those conjugates in which x, e, f, h, and y are each 1, and g is 1 or more and k is each individually 2 or more. Most preferred are those conjugates in which x, e, f, h, y, and g are each 1, and k is 2 or more. Also particularly 35 preferred are those starburst conjugates in which "Antibody" represents a monoclonal antibody or an epitope binding fragment thereof; and especially preferred are those in which M represents a bioactive agent such as a radionuclide, drug, or toxin.

The starburst conjugates can be used for a variety of in vitro or in vivo diagnostic applications such as radioimmunoassays, electron microscopy, enzyme linked immunosorbent assays, nuclear magnetic resonance spectroscopy, contrast imaging, and immunoscintography, in analytical applications, in therapeutic applications as a carrier of antibiotics, radionuclides, drugs or other agents suitable for use in the treatment of disease states such as cancer, autoimmune diseases, central nervous system disorders, infectious diseases, and cardiac disorders; in biological control applications as a means of delivering pesticides such as herbicides, fungicides, repellants, attractants, antimicrobials or other toxins; or used as starting materials for making other useful agents.

The present invention is also directed to starburst conjugate compositions in which the starburst conjugates are formulated with other suitable vehicles. The starburst conjugate compositions may optionally contain other active ingredients, additives and/or diluents.

In the agricultural materials embodiment of the invention, the starburst conjugates can be formulated with suitable vehicles useful in agriculture such as on crops, fallow land, or as pesticides, or in treatment of in vivo or in vitro testing of non-mammals. An agriculturally acceptable carrier or diluent which may also be present with one or more starburst conjugates of the present invention includes those carriers or diluents customarily used in granular formulations, emulsifiable concentrates, solutions, or suspensions such as, for example, toluene, xylene, benzene, phenol, water, methane, hydrocarbons, naphthalene and others.

The preferred starburst polymer for use in the starburst conjugates of the present invention is a polymer that can be described as a starburst polymer having at least one branch (hereinafter called a core branch), preferably two or more branches, emanating from a core, said branch having at least one terminal group provided that (1) the ratio of terminal groups to the core branches is more than one, preferably two or greater, (2) the density of terminal groups per unit volume in the polymer is at least 1.5 times that of an extended conventional star polymer having similar core and monomeric moieties and a comparable molecular weight and number of core branches, each of such branches of the extended conventional star polymer bearing only one terminal group, and (3) a molecular volume that is no more than about 80 percent of the molecular volume of said extended conventional star polymer as determined by dimensional studies using scaled Corey-Pauling molecular models. As used herein, the term "dense" as it modifies "star polymer" or "dendrimer" means that it has a smaller molecular volume than an extended conventional star polymer having the same molecular weight. The extended conventional star polymer which is used as the base for comparison with the dense star polymer is one that has the same molecular weight, same core and monomeric components and same number of core branches as the dense star polymer. By "extended" it is meant that the individual branches of the conventional star polymer are extended or stretched to their maximum length, e.g., as such branches exist when the star polymer is completely solvated in an ideal solvent for the star polymer. In addition while the number of terminal groups is greater for the dense star polymer molecule than in the conventional star polymer molecule, the chemical structure of the terminal groups is the same.

Dendrimers used in the conjugates of the present invention can be prepared by processes known in the art. The above dendrimers, the various coreactants and core compounds, and process for their preparation a can be as defined in U.S. Pat. No. 4,587,329.

The dendrimers, for use in the conjugates of the present invention, can have terminal groups which are sufficiently reactive to undergo addition or substitution reactions. Examples of such terminal groups include amino, hydroxy, mercapto, carboxy, alkenyl, allyl, vinyl, amido, halo, urea, oxiranyl, aziridinyl, oxazolinyl, imidazolinyl, sulfonato, phosphonato, isocyanato and isothiocyanato. The terminal groups can be modified to make them biologically inert, for example, to make them non-immunogenic or to avoid non-specific uptake in the liver, spleen or other organ. The dendrimers differ from conventional star or starbranched polymers in that the dendrimers have a greater concentration of terminal groups per unit of molecular volume than do conventional extended star polymers having an equivalent number of core branches and an equivalent core branch length. Thus, the density of terminal groups per unit volume in the dendrimer usually is at least 1.5 times the density of terminal groups in the conventional extended star polymer, preferably at least 5 times, more preferably at least 10 times, most preferably from 15 to 50 times. The ratio of terminal groups per core branch in the dense polymer is preferably at least 2, more preferably at least 3, most preferably from 4 to 1024. Preferably, for a given polymer molecular weight, the molecular volume of the dense star polymer is less than 70 volume percent, more preferably from 16 to 60, most preferably from 7 to 50 volume percent of the molecular volume of the conventional extended star polymer.

Preferred dendrimers for use in the conjugates of the present invention are characterized as having a univalent or polyvalent core that is covalently bonded to dendritic branches. Such ordered branching can be illustrated by the following sequence wherein G indicates the number of generations:

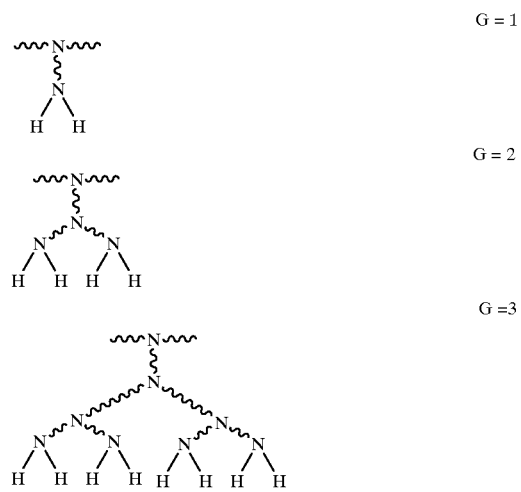

Mathematically, the relationship between the number (#) of terminal groups on a dendritic branch and the number of generations of the branch can be represented as follows:

$$\# \text{ of terminal groups per dendritic branch} = \frac{N_r^G}{2}$$

wherein G is the number of generations and $N_r$ is the repeating unit multiplicity which is at least 2 as in the case of amines. The total number of terminal groups in the dendrimer is determined by the following:

$$\# \text{ of terminal groups per dendrimer} = \frac{N_c N_r^G}{2}$$

wherein G and $N_r$ are as defined before and $N_c$ represents the valency (often called core functionality) of the core compound. Accordingly, the dendrimers of this invention can be represented in its component parts as follows:

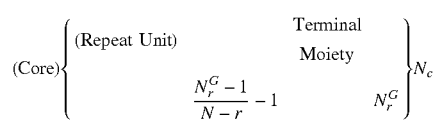

wherein the Core, Terminal Moiety, G and $N_c$ are as defined before and the Repeat Unit has a valency or functionality of $N_r+1$ wherein $N_r$ is as defined before.

A copolymeric dendrimer which is a preferred dendrimer for the purposes of this invention is a unique compound constructed of polyfunctional monomer units in a highly branched (dendritic) array. The dendrimer molecule is prepared from a polyfunctional initiator unit (core compound), polyfunctional repeating units and terminal units which may be the same or different from the repeating units. The core compound is represented by the formula I $(Z^c)_{N_c}$ wherein I represents the core, $Z^c$ represents the functional groups bonded to I and Nc represents the core functionality which is preferably 2 or more, most preferably 3 or more. Thus, the dendrimer molecule comprises a polyfunctional core, I, bonded to a number $(N_c)$ of functional groups, $Z^c$, each of which is connected to the monofunctional tail of a repeating unit, $X^1Y^1(Z^1)_{N}1$, of the first generation and each of the Z groups of the repeating unit of one generation is bonded to a monofunctional tail of a repeating unit of the next generation until the terminal generation is reached.

In the dendrimer molecule, the repeating units are the same within a single generation, but may differ from generation to generation. In the repeating unit, $X^1Y^1(Z^1)_{N}1$, $X^1$ represents the monofunctional tail of the first generation repeating unit, $Y^1$ represents the moiety constituting the first generation, $Z^1$ represents the functional group of the polyfunctional head of the repeating unit of the first generation and may be the same as or different from the functional groups of the core compound, I $(Z^c)_{N_c}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^iY^i(Z^i)_{N}i$ wherein "i" represents the particular generation from the first to the t−1 generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^iY^i(Z^i)_{N}i$ in generation number "i" is connected to the tail $(X^{i+1})$ of the repeating unit of the generation number "i+1". The final or terminal of a preferred dendrimer molecule comprises terminal units, $X^tY^t(Z^t)_{N}t$ wherein t represents terminal generation and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one. Therefore, the preferred dendrimer has a molecular formula represented by $$\left(\textcircled{I}(Z^c)_{N_c}\right)\left\{\left(X^iY^i(Z^i)_{N^i}\right)_{N_c\prod_{n\ is\ 1}^{i-1}N^n}\right\}\left(X^tY^t(Z^t)_{N^t}\right)_{N_c\prod_{n\ is\ 1}^{t-1}N^n}$$

where $i$ is 1 to $t-1$ wherein the symbols are as previously defined. The $\pi$ function is the product of all the values between its defined limits. Thus $$\prod_{n=1}^{i-1} N^n = (N^1)(N^2)(N^3)\cdots(N^{i-2})(N^{i-1})$$

which is the number of repeat units, $X^iY^i(Z^i)_{N}i$, comprising the ith generation of one dendritic branch and when i is 1, then $$\prod_{n=1}^{o} = 1.$$

In copolymeric dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of hydroxyl in the terminal generation to ester by reaction with an acid chloride gives an ester terminally functionalized dendrimer. This functionalization need not be carried out to the theoretical maximum as defined by the number of available functional groups and, thus, a functionalized dendrimer may not have high symmetry or a precisely defined molecular formula as is the case with the preferred dendrimer.

In a homopolymeric dendrimer, all of the repeat units, $X^iY^i(Z^i)_{N}i$, are identical. Since the values of all $N^i$ are equal (defined as $N_r$) the product function representing the number of repeat units reduces to a simple exponential form. Therefore, the molecular formula may be expressed in simpler form as:

$$\left(\textcircled{I}(Z^c)_{N_c}\right)\left\{\left(X^iY^i(Z^i)_{N^i}\right)_{N_cN_r^{i-1}}\right\}\left(X^tY^t(Z^t)_{N^t}\right)_{N_cN_r^{t-1}}$$

where $i$ = 1 to $t-1$

This form still shows the distinction between the different generations i, which each consist of $N_cN_r^{(i-1)}$ repeating units, $X^iY^i(Z^i)_{N}i$. Combining the generations into one term gives:

$$\left(\textcircled{I}(Z^c)_{N_c}\right)\left(X^rY^r(Z^r)_{N_r}\right)_{N_c\frac{N_r^{(t-1)}-1}{N_r-1}}\left(X^tY^t(Z^t)_{N^t}\right)_{N_cN_r^{(t-1)}}$$

or $$\left(\textcircled{I}(Z^c)_{N_c}\right)\left\{\left(X^rY^r(Z^r)_{N_r}\right)_{\frac{N_r^{(t-1)}-1}{N_r-1}}(X^tY^t(Z^t)_{N^t})_{N_r^{(t-1)}}\right\}_{N_c}$$

Core    Repeat Unit    Terminal Unit wherein $X^rY^r(Z^r)_{N_r}$ is the repeating unit which is used in all generations i.

Consequently, if a polymer compound will fit into these above formulae, then the polymer is a starburst polymer. Conversely, if a polymer compound will not fit into these above formulae, then the polymer is not a starburst polymer. Also, to determine whether a polymer is a starburst polymer, it is not necessary to know the process by which it was prepared, but only whether it fits the formulae. The formulae also demonstrate the generations (G) or tiering of dendrimers.

Clearly, there are several ways to determine the ratio of agent (M) to dendrimer (P) which depend upon how and where the association of P*M occurs. When there is interior encapsulation, the weight ratio of M:P usually is 10:1, preferably 8:1, more preferably 5:1, most preferably 3:1. The ratio can be as low as 0.5:1 to 0.1:1. When interior stoichiometry is used, the weight ratio of M:P is the same as for interior encapsulation. When exterior stoichiometry is determined, the mole/mole ratio of M:P is given by the following formulae:

| M | P |
|---|---|
| (A) 5 $N_cN_tN_r^{G-1}$ | 1 |
| (B) 3 $N_cN_tN_r^{G-1}$ | 1 |
| (C) 1 $N_cN_tN_r^{G-1}$ | 1 | where $N_c$ means the core multiplicity, $N_t$ means the terminal group multiplicity, and $N_r$ means branch juncture multiplicity. The $N_cN_tN_r^{G-1}$ term will result in the number of Z groups. Thus, for example, (A) above may result when proteins, enzymes or highly charged molecules are on the surface; (B) above when it is aspirin, 2,4-D or octanoic acid; (C) above when converting surface ester groups to carboxylate ions or groups.

Figure 3:
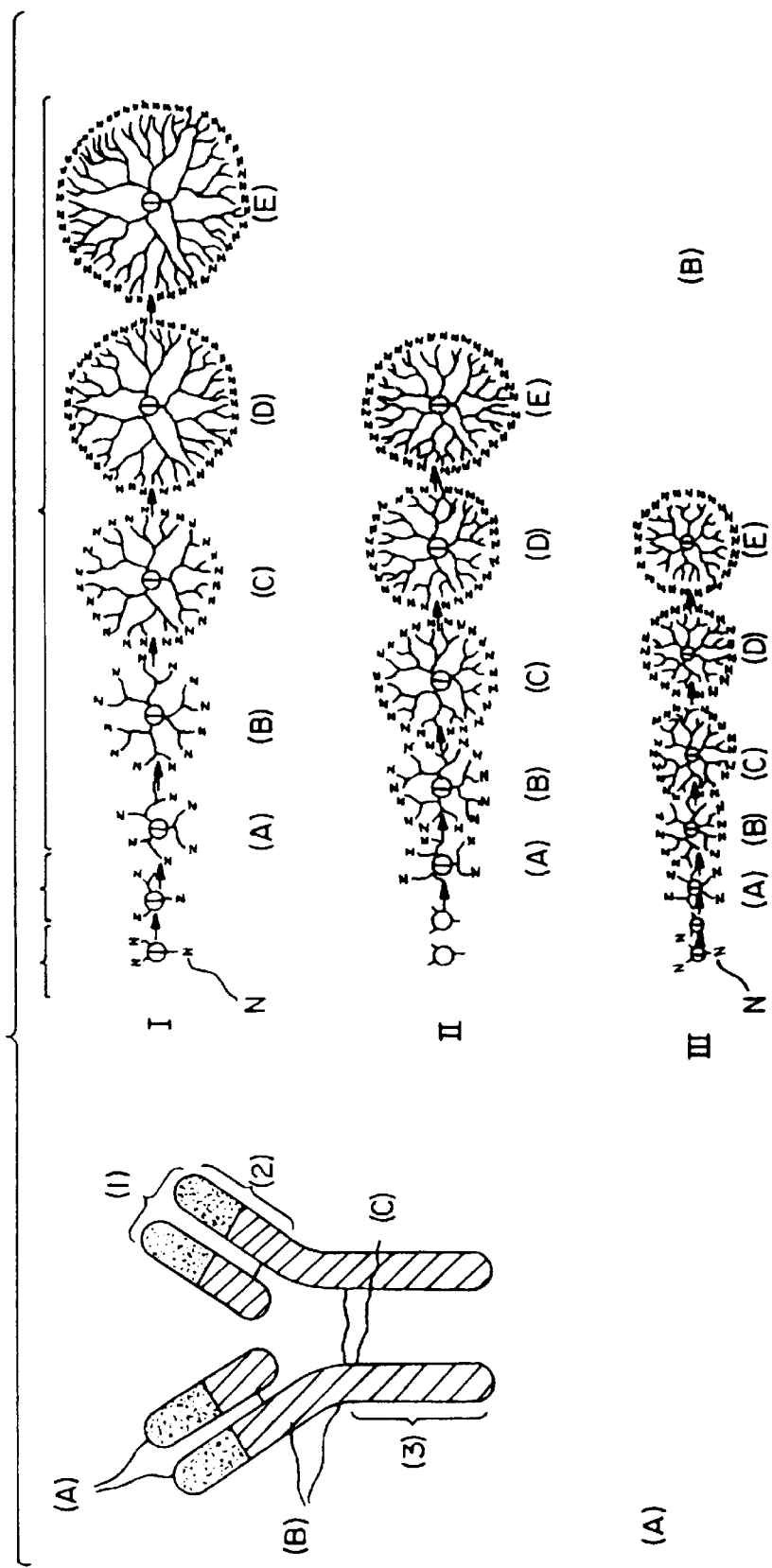
FIG. 3 depicts dendrimer sizes relative to antibody dimensions.

Of course other structures of various dimensions can be readily prepared by one skilled in the art by appropriately varying the dendrimer components and number of generations employed. A roughly scaled comparison of three different dendrimer series relative to an IgG antibody is seen in FIG. 3. The series of drawings indicated by FIG. 3(B) I shows the starburst polyamidoamines (PAMAM); by II shows the starburst polyethers (PE); and by III shows the starburst polyethyleneimines (PEI). In a manner similar to that of FIG. 1, all three series (I, II and III) have their far left drawing showing the initiator core, the next drawing from the left showing the starbranch oligomer, and the remaining drawings showing the starburst oligomers, and respective starburst bridged dendrimers. It can be seen that in these series of scale drawings that the dendrimer dimensions are close to and in fact smaller than those noted for the whole IgG antibody FIG. 3(A). The IgG antibody is shown to the far left in FIG. 3. The scale is 1 mm=3.5 Å. In FIG. 3(A) the variable region is shown by (A); the constant region by (B); and the carbohydrate attachment sites by (C). Approximate measurements shown on FIG. 3 are (1) is 35–40 Å; (2) is 70 Å; and (3) is 60 Å. These dimensional properties are preferred for instance where targeting involves exiting from the vascular system. Therefore dendrimer diameters of 125 Angstrom units or less are particularly preferred in that they may allow exiting from the vascular system to targeted organs serviced by continuous or fenestrated capillaries. These dimensions are significant in that they are small compared to the size of a potential targeting component such as an antibody (see FIG. 3). A linear polymer of comparable molecular weight would have a radius of gyration, (in its fully extended form), that would be much larger than the same molecular weight dendrimer. A linear polymer of this type would be expected to adversely affect the molecular recognition properties of many accepted targeting components. It is also desirable that the conjugates be of minimum molecular volume so as not to discourage extravasation, e.g., by coupling Fab, Fab' or other appropriate antibody fragment to low molecular volume dendrimers.

Dendrimers are desirable for the delivery of radionuclides or strongly paramagnetic metal ions to tumor sites because of their ability to chelate a number of metal ions in a small volume of space. Coupling to antibodies or antibody fragments which are specific for tumors may deliver a number of metals per antibody, with only a single modification to the antibody.

Linking target directors to dendrimers is another aspect of the present invention. In preferred embodiments of the present invention, particularly where it is desired to use an antibody as a target director, a reactive functional group such as a carboxyl, sulfhydryl, reactive aldehyde, reactive olefinic derivative, isothiocyanato, isocyanato, amino, reactive aryl halide, or reactive alkyl halide can conveniently be employed on the dendrimer. The reactive functional groups can be introduced to the dendrimer using known techniques, for example:

(1) Use of a heterofunctional initiator (as a starting material for synthesizing the dendrimer) which has incorporated into it functional groups of different reactivity. In such heterofunctional initiator at least one of the functional groups will serve as an initiation site for dendrimer formation and at least one of the other functional groups will be available for linking to a target director but unable to initiate dendrimer synthesis. For example, use of protected aniline allows further modification of $NH_2$ groups within the molecule, without reacting the aniline $NH_2$.

The functional group which will be available for linking to a target director may be part of the initiator molecule in any one of three forms; namely:

(a) In the form in which it will be used for linking with the target director. This is possible when none of the synthetic steps involved in the dendrimer synthesis can result in reaction at this center.

(b) When the functional group used for linking to the targeting director is reactive in the synthetic steps involved in the dendrimer synthesis, it can be protected by use of a protecting group, which renders the group unreactive to the synthetic procedures involved, but can itself be readily removed in a manner which does not alter the integrity of the remainder of the macromolecule.

(c) In the event that no simple protecting group can be formed for the reactive functionality to be used for linking with the targeting director, a synthetic precursor can be used which is unreactive in all the synthetic procedures used in the dendrimer synthesis. On completion of the synthesis, this functional group must be readily convertible into the desired linking group in a manner which does not alter the integrity of the remainder of the macromolecule.

(2) Coupling (covalently) the desired reactive functional group onto a preformed dendrimer, the reagent used must contain a functionality which is readily reacted with the terminal functional groups of the dendrimer. The functional group to be ultimately used to link with the targeting agent can be in its final form, as a protected functionality, or as a synthetic precursor. The form in which this linking functionality is used depends on its integrity during the synthetic procedure to be utilized, and the ability of the final macromolecule to withstand any conditions necessary to make this group available for linking. For example, the preferred route for PEI uses

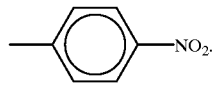

Examples of heterofunctional initiators for use in (1) above, include the following illustrative examples:

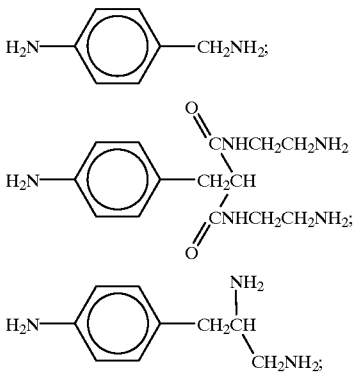

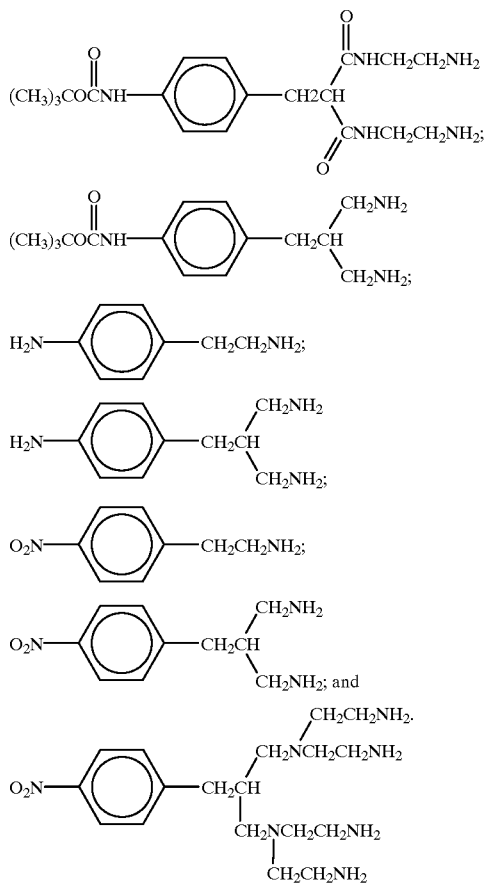

There are several chemistries of particular importance:
1) Starburst Polyamidoamines ("PAMAM") Chemistry;
2) Starburst Polyethyleneimines ("PEI") Chemistry;
3) Starburst PEI compound with a surface of PAMAM;
4) Starburst polyether ("PE") chemistry.

Modifications of the dendrimer surface functionalities may provide other useful functional groups such as the following:
—$OPO_3H_2$, —$PO_3H_2$, —$PO_3H^{(-1)}$, —$PO_3^{(-2)}$, —$CO_2^{(-1)}$, —$SO_2H$, —$SO_2^{(-1)}$, —$SO_3H$, —$SO_3^{(-1)}$, —$NR^1R^2$, —$R^5$, —OH, —$OR^1$, —$NH_2$, polyethers, perfluorinated alkyl,

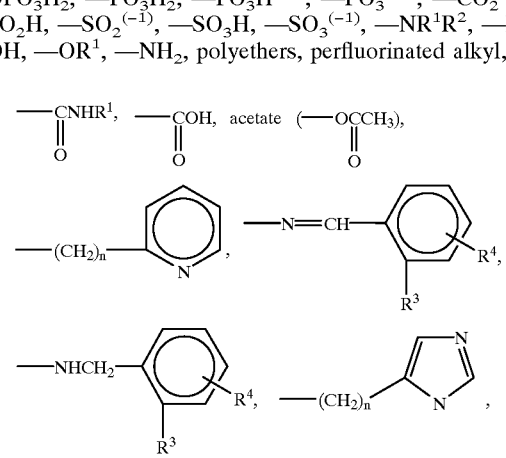

wherein
R represents alkyl, aryl or hydrogen;

$R^1$ represents alkyl, aryl, hydrogen, or

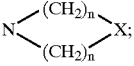

$R^2$ represents alkyl, aryl, or

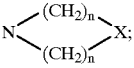

$R^3$ represents —OH, —SH, —$CO_2H$, —$SO_2H$, or —$SO_3H$;
$R^4$ represents alkyl, aryl, alkoxy, hydroxyl, mercapto, carboxyl, nitro, hydrogen, bromo, chloro, iodo, or fluoro;
$R^5$ represents alkyl;
X represents NR, O or S; and
n represents the integer 1, 2 or 3;
polyethers; or other immuno insensitive moieties
wherein for all the above, alkyl is a linear or branched $C_1$–$C_{18}$ hydrocarbon and aryl is a benzyl or napthyl which may be substituted with one or more $C_1$–$C_4$ alkyl, bromo, chloro, iodo, fluoro, or trifluoromethyl moieties.

The choice of functional group depends upon the particular end use for which the dendrimer is designed. For example, a dendrimer having 1,4,7,10-tetraazacyclododecane-1,4,7,10-tetraacetic acid (DOTA) or 1,4,7-tris-(carbomethoxymethyl)-1,4,7,10-tetraazacyclodocecane (DO3A methyl ester) as the functional group can be used as carriers for magnetic resonance imaging or as nuclear magnetic resonance reagents.

These fuctionalized dendrimers are prepared, for example, by reacting the functionalizing group, such as DO3A methyl ester, with an epoxide or epoxide substituted with a $C_1$–$C_{18}$ alkyl group to form a hydroxyethylated product. The hydroxyethylated product is reacted with a coupling agent, such as dicyclohexyl carbodiimide (DCC), and then reacted with a PAMAM starburst polymer. A dendrimer having DOTA as a functional group can be prepared by using an isothiocyanate derivatized DOTA, such as, 1-[1-carboxy-3(4'-isothiocyanatophenyl)propyl]-4,7,10-tris(carboxymethyl)-1,4,7,10-tetraazacyclododecane, with a PAMAM starburst polymer. Other suitable chelates can be added by known synthetic techniques. When desired, a lanthanide ion or pseudolanthanide ion can be incorporated by conventional methods.

Linking of antibodies to dendrimers is another aspect of the present invention. Typically, the antibodies or antibody fragments are linked to the dendrimer by techniques well known in the art such as attachment between a functional group on the dendrimer and moieties such as carbohydrate, amino, carboxyl, or sulfhydryl functionalities present in the antibody or antibody fragment. In some instances connecting groups may be used as connectors or spacers between the dendrimer and antibody or antibody fragment. The attachment of the dendrimer to the antibody or antibody fragment should be performed in a manner which does not significantly interfere with the immunoreactivity of the antibody or antibody fragment, that is, by binding the antibody or antibody fragment via a functionality in the antibody or antibody fragment which is not a part of the antigen recognition and binding site.

The following examples further illustrate the invention but are not to be construed as a limitation on the scope of the invention. The lettered examples concern the preparation of starting materials; the numbered examples concern the preparation of products.

EXAMPLE A

Preparation of 2-Carboxamido-3-(4'-nitrophenyl) propanamide p-Nitrobenzyl malonate diethylester (2.4 grams (g), 8.13 mmole) was dissolved in 35 ml of methanol. The solution was heated to 50–55° C. with stirring and a stream of anhydrous ammonia was bubbled through the solution for 64 hours. The solution was cooled and the white, flocculant product was filtered and recrystallized from 225 milliliters (ml) of boiling methanol to afford 1.85 g (7.80 mmole) of bis amide in 96% yield (mp=235.6° C. (d).

The structure was confirmed by MS, $^1$H and $^{13}$C NMR spectroscopy.

| Anal: Calc. for $C_{10}H_{11}O_4N_3$ | | | |
|---|---|---|---|
|  | C | H | N |
| Theo: | 50.63 | 4.69 | 17.72 |
| Found: | 50.75 | 4.81 | 17.94 |

EXAMPLE B

Preparation of 1-Amino-2-(aminomethyl)-3-(4'-nitrophenyl)propane

2-Carboxamido-3-(4'-nitrophenyl)propanamide (2.0 g, 8.43 mmole) was slurried in 35 ml of dry tetrahydrofuran under a nitrogen atmosphere with stirring. To this mixture was added borane/tetrahydrofuran complex (106 ml, 106 mmole) via syringe. The reaction mixture was then heated to reflux for 48 hours during which time the suspended amide dissolved. The solution was cooled and the tetrahydrofuran was removed in vacuo using a rotary evaporator. The crude product and borane residue was dissolved in 50 ml of ethanol and this solution was purged with anhydrous hydrogen chloride gas. The solution was refluxed for 1 hour and the solvent removed in vacuo. The crude hydrochloride salt was dissolved in 15 ml of deionized water and extracted with two 50 ml portions of methylene chloride. The aqueous layer was cooled in an ice bath under an argon blanket and 50% sodium hydroxide was slowly added until basic pH=11.7. The basic aqueous layer was extracted with four 25 ml portions of methylene chloride and these combined extracts were evaporated (rotary) to give 1.45 g of amber colored oil. This oil was triturated with diethyl ether (50 ml) and filtered under pressure through a short silica gel (grade 62 Aldrich) column. The column was washed with 100 ml of ether and the combined filtrates were vacuum evaporated giving 1.05 g (5.02 mmole) of the titled diamine as a clear oil (mp=275–278° C.(d) bis HCl salt)

The structure was confirmed by MS, $^1$H and $^{13}$C NMR spectroscopy.

| Anal: Calc. for $C_{10}H_{17}N_3O_2Cl_2$ | | | |
|---|---|---|---|
|  | C | H | N |
| Theo: | 42.57 | 6.07 | 14.89 |
| Found: | 43.00 | 6.14 | 15.31 |

EXAMPLE C

Preparation of 1-Amino-2-(aminomethyl)-3-(4'-aminophenyl)propane

Borane/tetrahydrofuran solution (70 ml, 70 mmole) was added under nitrogen via a cannula needle to a flask containing 4-amino-benzyl malonamide (1.5 g, 7.24 mmole) with stirring. The solution was brought to reflux for 40 hours. The colorless solution was cooled and excess tetrahydrofuran was removed by rotary evaporation leaving a clear gelatinous oil. Methanol (50 ml) was cautiously added to the oil with notable gas evolution. Dry hydrogen chloride was bubbled through the suspension to effect dissolution and the solution was then refluxed for 1 minute. The methanol/HCl was rotary evaporated and the resulting hydrochloride salt was carried through the same dissolution/reflux procedure again. The hydrochloride salt obtained was dissolved in 10 ml of water and cooled in an ice bath under argon. Concentrated sodium hydroxide (50%) was added slowly with stirring to pH=11. The aqueous portion was then extracted with 2×100 ml portions of chloroform which were combined and filtered through a short silica gel plug without drying. The solvent was removed in vacuo (rotary) affording the title compound (0.90 g, 5.02 mmole) in 70% yield ($R_f$=0.65—$CHCl_3/MeOH/NH_4OH$ conc—2/2/1). The structure was confirmed by $^1$H and $^{13}$C NMR and used without further purification.

EXAMPLE D

Preparation of 6-(4-Aminobenzyl)-1,4,8,11-tetraaza-5,7-dioxoundecane

4-Aminobenzyl malonate dimethylester (2.03 g, 8.43 mmole) was dissolved in 10 ml of methanol. This solution was added dropwise to a stirred solution of freshly distilled ethylene diamine (6.00 g, 103.4 mmole) in 10 ml of methanol under nitrogen over a 2 hour period. The clear solution was stirred for 4 days and Thin Layer Chromatography (TLC) analysis indicated total conversion of diester ($R_f$=0.91) to the bis amide ($R_f$=0.42–20% conc $NH_4OH/80\%$ ethanol). This material was strongly ninhydrin positive. The methanol and excess diamine were removed on a rotary evaporator and the resulting white solid was vacuum dried ($10^{-1}$ mm, 50° C.) overnight to afford crude product (2.45g, 8.36 mmole) in 99% yield. An analytical sample was recrystallized from chloroform/hexane, MP=160–161° C. The mass spectral, $^1$H and $^{13}$C NMR data were consistent with the proposed structure.

EXAMPLE

Reaction of Mesyl Aziridine with 1-Amino-2-(aminomethyl)-3-(4-nitrophenyl)propane 1-Amino-2-(aminomethyl)-3-(4-nitrophenyl)propane (400 mg, 1.91 mmole, >96% pure) was dissolved in 10.5 ml of absolute ethanol under nitrogen. Mesyl aziridine (950 mg, 7.85 mmole) was added to the stirred diamine solution as a solid. The reaction was stirred at 25° C. for 14 hours using a magnetic stirrer and during this period a white, gummy residue formed on the sides of the flask. The ethanol was decanted and the residue was triturated with another 15 ml portion of ethanol to remove any unreacted aziridine. The gummy product was vacuum dried ($10^1$ mm, 25° C.) to afford the tetrakis methyl sulfonamide (1.0 g, 1.44 mmole) in 75% yield ($R_f$=0.74—$NH_4OH/ethanol$—20/80). The structure was confirmed by $^1$H and $^{13}$C nuclear magnetic resonance (NMR) spectroscopy.

EXAMPLE F

Preparation of 2-(4-Nitrobenzyl)-1,3-(bis-N,N-2-aminoethyl)diaminopropane

The crude methylsulfonamide (650 mg, 0.94 mmole) was dissolved in 5 ml of nitrogen purged, concentrated sulfuric acid (98%). This solution was maintained under nitrogen and heated to 143–146° C. for 27 minutes with vigorous stirring. A slight darkening was noted and the cooled solution was poured into a stirred solution of ether (60 ml). The precipitated white salt cake was filtered and immediately dissolved in 10 ml of deionized water. The pH of the solution was adjusted to pH=11 with 50% NaOH under argon with cooling. The resulting solution was mixed with 90 ml of ethanol and the precipitated inorganic salts were filtered. The solvent was removed from the crude amine under reduced pressure and to the resulting light brown oil was added 190 ml of toluene under nitrogen. The mixture was stirred vigorously and water was removed through azeotropic distillation (Dean-Stark trap) until the remaining toluene acquired a light yellow color (30–40 ml remaining in pot). The toluene was cooled and decanted from the dark, intractable residues and salt. This solution was stripped of solvent in vacuo and the resulting light yellow oil was vacuum dried (0.2 mm, 35° C.) overnight affording 210 mg of the product (60%) which was characterized by MS, $^1$H and $^{13}$C NMR.

EXAMPLE G

Preparation of a Starburst Polymer (Containing an Aniline Derivative) of One Half Generation Represented by the Following Scheme

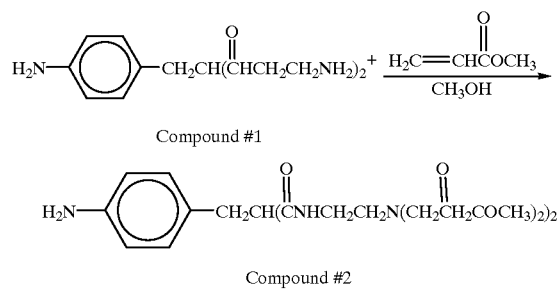

Methyl acrylate (2.09 g, 24 mmole) was dissolved in methanol (15 ml). The compound 6-(4aminobenzyl)-1,4,8,11-tetraaza-5,7-dioxoundecane (1.1 g, 3.8 mmole) (i.e., Compound #1, the preparation of this compound is shown in Example D) was dissolved in methanol (10 ml) and was added slowly over 2 hours with rigorous stirring to the methyl acrylate solution. The reaction mixture was stirred for 48 hours at ambient temperatures. The solvent was removed on the rotary evaporator maintaining the temperature below 40° C. The ester (Compound #2) was obtained as a yellow oil (2.6 g). No carboxyethylation of the aniline function was observed.

EXAMPLE H

Preparation of a Starburst Polymer (Containing an Aniline Moiety) of One Generation; Represented by the Following Scheme

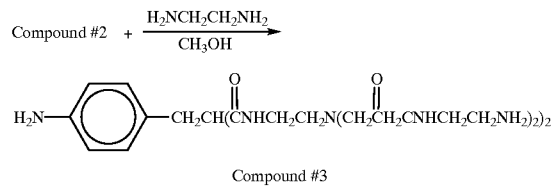

The ester (Compound #2) (2.6 g, 3.7 mmole) was dissolved in methanol (100 ml). this was carefully added to a vigorously stirring solution of ethylene diamine (250 g, 4.18 mole) and methanol (100 ml) at such a rate that the temperature did not rise above 40° C. After complete addition the reaction mixture was stirred for 28 hours at 35–40° C. (heating mantle). After 28 hours no ester groups were detectable by infrared spectroscopy. The solvent was removed on the rotary evaporator at 60° C. The excess ethylene diamine was removed using a ternary azeotrope of toluene-methanol-ethylene diamine. Finally all remaining toluene was azeotroped with methanol. Removal of all the methanol yielded 3.01 g of the product (Compound #3) as an orange glassy solid.

EXAMPLE I

Preparation of a Starburst Polymer (Containing an Aniline Moiety) of One and One Half Generations Represented by the Following Scheme

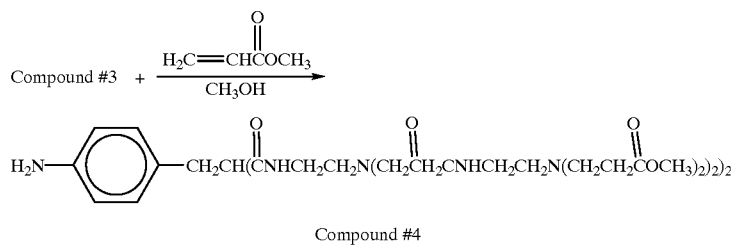

The amine (Compound #3) (2.7 g, 3.6 mmole) was dissolved in methanol (7 ml) and was added slowly over one hour to a stirred solution of methyl acrylate (3.8 g, 44 mmole) in methanol (15 ml) at ambient temperatures. A slight warming of the solution was observed during the addition. The solution was allowed to stir at ambient temperatures for 16 hours. The solvent was removed on the rotary evaporator at 40° C. After removal of all the solvent and excess methyl acrylate the ester (Compound #4) was obtained in 4.7 g yield as an orange oil.

EXAMPLE J

Preparation of a Starburst Polymer (Containing an Aniline Moiety) of One Half Generation Represented by the Following Scheme

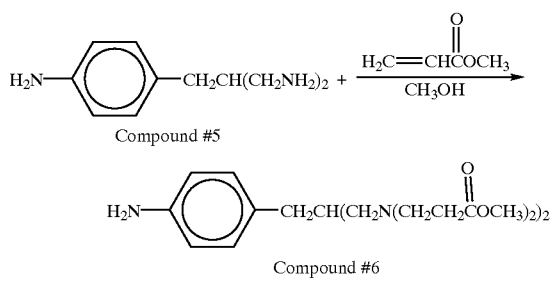

Compound #5

Compound #6

The triamine (Compound #5, the preparation of this compound is shown in Example C) (0.42 g, 2.3 mmole) was dissolved in methanol (10 ml) and was added dropwise over one hour to methyl acrylate (1.98 g, 23 mmole) in methanol (10 ml). The mixture was allowed to stir at ambient temperatures for 48 hours. The solvent was removed on the rotary evaporator, maintaining the temperature at no higher than 40° C. The excess methyl acrylate was removed by repeated azeotroping with methanol. The ester (Compound #6) was isolated as an orange oil (1.24 g).

EXAMPLE K

Preparation of a Starburst Polymer (Containing an Aniline Moiety) of One Generation; Represented by the Following Scheme

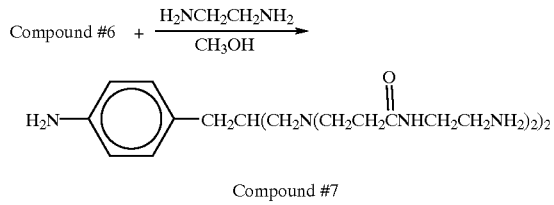

Compound #7

The ester (Compound #6) (1.24 g, 2.3 mmole) was dissolved in methanol (50 ml) and was added dropwise over two hours to ethylenediamine (73.4 g, 1.22 mole) in methanol (100 ml). A small exotherm was noted, vigorous stirring was maintained. The solution was left to stir at ambient temperatures for 72 hours. The solvent was removed on the rotary evaporator at 60° C. The excess ethylene diamine was removed using a ternary azeotrope of toluene-methanol-ethylenediamine. Finally all remaining toluene was removed with methanol and then pumping down with a vacuum pump for 48 hours gave the amine (Compound #7) (1.86 g) as a yellow/orange oil.

EXAMPLE L

Preparation of a Starburst Polymer (Containing an Aniline Moiety) of One and One Half Generations; Represent by the Following Scheme

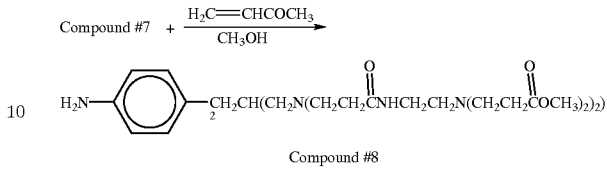

Compound #8

The amine (Compound #7) (1.45 g, trace of methanol remained) was dissolved in methanol (100 ml) and was added slowly over 1 hours to a stirred solution of methyl acrylate (5.80 g) in methanol (20 ml). The solution was allowed to stir for 24 hours at room temperature. Removal of the solvent followed by repeated azeotroping with methanol enabled the removal of all the excess methyl acrylate. After pumping down on a vacuum pump for 48 hours the ester (Compound #8) was isolated as an orange oil (2.50 g, 1.8 mmole).

EXAMPLE M

Hydrolysis of 4.5 Generation Dendrimer and Preparation of Calcium Salt 4.5 Generation PAMAM (ester terminated, initiated off $NH_3$) (2.11 g, 10.92 meq) was dissolved in 25 ml of methanol and to it was added 10% NaOH (4.37 ml, 10.92 meq) (pH=11.5–12). After 24 hours at room temperature, the pH was about 9.5. After an additional 20 hours, the solution was rotovaped (rotary evaporated), 50 ml of toluene added, and rotovaped again.

The resulting oil was dissolved in 25 ml of methanol and precipitated as a white gum upon addition of 75 ml of diethyl ether. The liquid was decanted, and the gum was rotovaped to give a very fine off-white powder which upon further drying gives 2.16 g of product (98% yield). No ester groups were found upon NMR and infrared analysis.

The sodium salt of 4.5 Generation PAMAM (ester terminated, initiated from $NH_3$) was replaced by the calcium salt via dialysis. The sodium salt (1.03 g) was dissolved in 100 ml of water and passed through hollow fiber dialysis tubing (cut off=5000) at 3 ml/minute. The exterior of the tubing was bathed in 5% $CaCl_2$ solution. This procedure was then repeated.

The resulting solution was again dialyzed, this time against water, then repeated two additional times.

Evaporation provided 0.6 g of wet solid, which was taken up in methanol (not totally soluble) and is dried to give 0.45 g of off-white crystals.

$C_{369}H_{592}O_{141}N_{91}Ca_{24}$ Calc.—10.10% $Ca^{++}$

M Wt.=9526.3 Calc.=C,4432.1; H,601.8; O,2255.9; N,1274.6; Ca,961.9).

| Theo: | C-46.5, | H-6.32, | N-13.38, | Ca-10.10 |
|---|---|---|---|---|
| Found: | C-47.34, | H-7.00, | N-13.55, | Ca-8.83 |

EXAMPLE N

Preparation of Dendrimers with Terminal Carboxylate Groups

Half-generation starburst polyamidoamines were hydrolyzed to convert their terminal methyl ester groups to carboxylates. This generated spheroidal molecules with negative charges dispersed on the periphery. The dendrimers hydrolyzed ranged from 0.5 generation (three carboxylates) to 6.5 generation (192 carboxylates).

The products could be generated as $Na^+$, $K^+$, $Cs^+$ or $Rb^+$ salts.

EXAMPLE O

N-t-butoxycarbonyl-4-aminobenzyl malonate dimethylester

4-Aminobenzyl malonate dimethylester (11.62 g, 49 mmol) was dissolved in 50 ml of t-butanol:water (60:40 with stirring. Di-t-butoxydicarbonate (19.79 g, 90 mmol) was added and the reaction mixture stirred overnight. The butanol was removed on the rotary evaporator, resulting in a yellow suspension of the product in water. Extraction into methylene chloride, drying ($MgSO_4$) and evaporation gave a yellow oil (21.05 g, contaminated by di-t-butoxydicarbonate). Recrystallization from 2-propanol:water (75:25) yield pale yellow crystals (11.1 g, 33 mmol, 67%). The structure was confirmed by $13_C$ NMR and purity checked by HPLC analysis (Spherisorb ODS-1, 0.05M $H_3PO_4$ pH 3: $CH_3CN$ 55:45). The material was used without further purification.

EXAMPLE P

N-t-butoxycarbonyl-6-(4-aminobenzyl)-1,4,8,11-tetraaza-5,7-dioxoundecane

N-t-butoxycarbonyl-4-aminobenzyl malonate dimethylester (8.82 g 26 mmol), prepared in Example O, was dissolved in 50 ml of methanol, This solution was added dropwise (2 hours) to a solution of freshly distilled ethylenediamine (188 g 3.13 mole) and 20 ml of methanol, under a nitrogen atmosphere. The solution was allowed to stir for 24 hours. The ethylene diamine/methanol solution was removed on the rotary evaporator. The product was dissolved in methanol and toluene added. Solvent removal on the rotary evaporator gave the crude product as a white solid (10.70 g contaminated with ethylenediamine). The sample was divided into two samples for purification. Azeotropic removal of ethylenediamine with toluene, using a soxhlet extractor with sulphonated ion exchange beads in the thimble to trap the ethylenediamine, resulted in partial decomposition of the product, giving a brown oil. The remaining product was isolated as a white solid from the toluene on cooling (2.3 g approximately 50 percent). Analysis of a 10 percent solution in methanol by gas chromatography (Column, Tenax 60/80) showed no ethylenediamine detectable in the sample (<0.1 percent). The second fraction was dissolved in methanol to give a 10 percent solution (by weight) and purified from the ethylenediamine by reverse osmosis, using methanol as the solvent. (The membrane used was a Filmtec FT-30, in an Amicon TC1R thin channel separator, the ethylenediamine crossing the membrane.) The product was isolated as a white solid (2.7 g), in which no detectable amounts of ethylenediamine could be found by gas chromatography. The $^{13}C$ NMR data and HPLC analysis (Spherisorb ODS-1, 0.05M $H_3PO_4$ pH 3:$CH_3CN$ 55:45) were consistent with the proposed structure. The product was used with no further purification.

EXAMPLE Q

Preparation of a Starburst Dendrimer of One Half Generation from N-t-butoxycarbonyl-6-(4-aminobenzyl)-1,4,8,11-tetraaza-5,7-dioxoundecane N-t-butoxycarbonyl-6-(4-aminobenzyl)-1,4,8,11-tetraaza-5,7-dioxoundecane (5.0 g 13 mmol), prepared in Example P, was dissolved in 100 ml of methanol. Methyl acrylate (6.12 g, 68 mmol) was added and the solution stirred at ambient temperatures for 72 hours. The reaction was monitored by HPLC (Spherisorb ODS1, Acetonitrile: 0.04M Ammonium acetate 40:60) to optimize conversion to the desired product. The solution was concentrated to 30 percent solids, and methyl acrylate (3.0 g 32 mmol) was added. The reaction mixture was stirred at ambient temperatures until no partially alkylated products were detectable by HPLC (24 hours). Removal of the solvent at 30° C. by rotary evaporation, and pumping down at 1 mm Hg for 24 hours gave the product as yellow viscous oil, yield 7.81 g. The $^{13}C$ NMR data was consistent with the proposed structure. The product was used without further purification.

EXAMPLE R

Preparation of a Starburst Dendrimer of One Full Generation from N-t-butoxycarbonyl-6-(4-aminobenzyl)-1,4,8,11-tetraaza-5,7-dioxoundecane The half generation product (Example Q) (7.70 g, 10.45 mmol) was dissolved in 75 ml of methanol and added dropwise over 2 hours to a stirred solution of ethylenediamine (400 ml, 7.41 mol) and methanol (50 ml). The reaction mixture was stirred at ambient temperatures for 48 hours. The ethylenediamine and methanol were removed by rotary evaporation to give a yellow oil (11.8 g contaminated with ethylenediamine). The product was dissolved in 90 ml of methanol, and purified from the ethylenediamine by reverse osmosis (Filmtec FT-30 membrane and Amicon TC1R thin channel separator, methanol as solvent). After 48 hours, no ethylenediamine could be detected by gas chromatography (Column, Tenax 60/80). Removal of the solvent on the rotary evaporator, followed by pumping down on a vacuum line for 24 hours gave the product as a yellow glassy solid (6.72 g). Analysis by HPLC, PLRP-S column, acetonitrile:0.015M NaOH, 10–20 percent gradient in 20 min.) and $^{13}C$ NMR analysis was consistent with the proposed structure.

EXAMPLE S

Preparation of a Starburst Polymer of One and One Half Generation from N-t-butoxycarbonyl-6-(4-aminobenzyl)-1,4,8,11-tetraaza-5,7-dioxoundecane The one generation product (Example R) (2.14 g, 25 mmol) was dissolved in 12.5 ml of methanol, and methyl acrylate (3.5 g, 39 mmol) in 5 ml of methanol was added. The solution was stirred at ambient temperatures for 48 hours, monitoring the progress of the reaction by HPLC (Spherisorb ODS-1, acetonitrile: 0.04M ammonium acetate, 60:40). A second aliquot of methyl acrylate was added (3.5 g 39 mmol) and the reaction mixture stirred at ambient temperatures for a further 72 hours. Removal of the solvent on the rotary evaporator gave the product as a yellow oil (3.9 g) after pumping down overnight with a vacuum pump. The product was used with no further purification.

EXAMPLE T

Preparation of a Starburst Polymer of Two Full Generations from N-t-butoxycarbonyl-6-(4-aminobenzyl)-1,4,8,11-tetraaza-5,7-dioxoundecane The one and one half generation product (Example S) (3.9 g, 2.5 mmol) was dissolved in 50 ml of methanol, and was added dropwise over 2 hours to a stirred solution of ethylenediamine (600 g, 10 mol) and methanol (50 ml). The solution was stirred at ambient temperatures under an atmosphere of nitrogen for 96 hours. The ethylenediamine/methanol was removed on the rotary evaporator to give a yellow glassy solid (4.4 g contaminated with ethylenediamine). A 10 percent solution of the product was made in methanol, and purified from the ethylenediamine by reverse osmosis (membrane used as a Filmtec FT-30, in an Amicon TC1R thin channel separator) until no ethylenediamine could be detected by gas chromatography (Column, Tenax 60/80. Removal of the solvent gave the product as a yellow glassy solid (3.52 g). The $^{13}$C NMR data and HPLC analysis (PLRP-S column, acetonitrile:0.015 M NaOH, 10 to 20 percent gradient in 20 minutes, were consistent with the proposed structure.

EXAMPLE U

Reaction of the Two Generation Starburst with Bromoacetic Acid to Give a Methylene Carboxylate Terminated Starburst Dendrimer The second generation product (Example T) (0.22 g, 0.13 mmol) was dissolved in 15 ml of deionized water and the temperature equilibrated at 40.5° C. Bromoacetic acid (0.48 g, 3.5 mmol) and lithium hydroxide (0.13 g, 3.3 mmol) were dissolved in 5 ml of deionized water, and added to the reaction mixture. The reaction pH was carefully maintained at 9, with the use of a pH stat (titrating with 0.1N NaOH), at 40.5° C. overnight. Monitoring by reverse phase HPLC, (Spherisorb ODS-1 column, eluent 0.25 M $H_3PO_4$ pH 3 [NaOH]; acetonitrile 85:15) confirmed the synthesis of predominantly a single component.

EXAMPLE V

Preparation of Isothiocyanato Functionalized Second Generation Methylene-carboxylate Terminated Starburst Dendrimer Five ml of a 2.8 mM solution of the second generation methylenecarboxylate terminated starburst dendrimer (Example U) was diluted with 20 ml water and the pH adjusted to 0.5 with concentrated hydrochloric acid. After one hour at room temperature the mixture was analyzed by HPLC to verify the removal of the butoxycarbonyl group and then treated with 50 percent sodium hydroxide to bring the pH to 7. A pH stat (titrating with 0.1 N NaOH) was used to maintain the pH at 7 and 225 $\mu$l thiophosgene was added. After 15 minutes at room temperature the pH of the mixture was adjusted to 5 with 1N HCl. The mixture washed with chloroform (20 ml×2) then concentrated on a rotary evaporator at reduced pressure. The residue recovered 0.91 g is a mixture of the isothiocyanate and salts.

EXAMPLE W

Preparation of Second Generation Starburst Polyethyleneimine-methane Sulfonamide To a solution of 125 g N-methanesulfonyl-aziridine in 50 ml ethanol was added 25.0 g tris(2-aminoethyl)amine. The solution was stirred at room temperature for 4 days. Water was added to the reaction mixture as needed to maintain the homogeneity of the solution. The solvent was removed by distillation in vacuo to give the 2nd generation starburst PEI-methane sulfonamide as a yellow glass (161 g).

EXAMPLE X

Cleavage of Methane Sulfonamides to Form Second Generation Starburst Polyethyleneimine A solution of 5.0 g of second generation starburst PEI-methane sulfonamide, from Example W in 20 ml of 38 percent HCL was sealed in a glass ampoule. The ampoule was heated at 160° C. for 16 hours, then cooled in an ice bath and opened. The solvent was removed by distillation invacuo and the residue dissolved in water. After adjusting the pH of the solution to greater than or equal to 10 with 50 percent NaOH, the solvent was removed by distillation in vacuo. Toluene (150 ml) was added to the residue and the mixture heated at reflux under a Dean-Stark trap until no more water could be removed. The solution was filtered to remove salts and the filtrate concentrated invacuo to give 1.9 g second generation starburst PEI as a yellow oil.

EXAMPLE Y

Preparation of Third Generation Starburst Polyethyleneimine-methane Sulfonamide

To a solution of 10.1 g second generation starburst PEI, from Example X, in 100 ml ethanol was added 36.6 g N-methanesulfonylaziridine. The solution was stirred at room temperature for 1 week. Water was added as needed to maintain the homogeneity of the solution. The solvent was removed by distillation in vacuo to give third generation starburst PEI-methane sulfonamide as a yellow glass (45.3 g).

EXAMPLE Z

Cleavage of Methane Ssulfonamides to Form 3rd Generation Starburst Polyethyleneimine The methane sulfonamide groups of third generation starburst PEI-methane sulfonamide (5.0 g), from Example Y, were removed by the same procedure as described for the second generation material in Example X to give 2.3 g third generation starburst PEI as a yellow oil.

EXAMPLE AA

Reaction of a Third Generation Starburst Polyethyleneimine with 4-fluoro-nitrobenzene The third generation starburst polyethyleneimine (Example Z) (1.06 g, 1.2 mmol) was dissolved in 12 ml of absolute ethanol. (4-Fluoro)-nitrobenzene (120 $\mu$l, 1.2 mmol) was added and the reaction mixture refluxed overnight. The solvent was removed on the rotary evaporator, and the bright yellow oil dissolved in water. The aqueous solution was washed with chloroform to remove any unreacted (4-fluoro)-nitrobenzene. Removal of the water gave the product as a deep yellow oil (0.80 g). The $^{13}$C NMR spectrum was consistent with the proposed structure. (No attempt was made to determine the nature of the statistical distribution). The product was used without further purification.

EXAMPLE BB

Reaction of the Nitrophenyl Derivative of the Third Generation Starburst Polyethyleneimine with 2Glycolonitrile The nitrophenyl derivative of the third generation starburst polyethyleneimine (Example AA) (0.80 g) was dissolved in 20 ml of deionized water. Sodium hydroxide (2.80 g, 50 percent w/w) was added to the stirred solution, and the solution purged with nitrogen, venting through a sodium hydroxide scrubber. Glycolonitrile (2.85 ml of a 70 percent aqueous solution) was added at ambient temperatures. A yellow precipitate was observed to form after a few minutes.

After two hours, the temperature was slowly raised to a reflux, and the solution maintained at a reflux with a nitrogen purge for 24 hours. Removal of the water gave the product as a yellow solid contaminated with glycolic acid and sodium hydroxide. The $^{13}$C NMR spectrum was consistent with the proposed structure. The product was used without further purification.

EXAMPLE CC

Hydrogenation of the Nitrophenyl Derivative to the Aminophenyl Methylenecarboxylate Terminated Third Generation Starburst Polyethyleneimine The yellow solid from Example BB (1.70 g) was dissolved in 10 ml of deionized water, the resulting pH of the solution was approximately 11. Palladium on charcoal (200 mg of 5 percent Pd/C) was added to the reaction mixture in a glass Parr shaker bottle. The reaction mixture was placed under a pressure of 40 psi (275 kPa) of hydrogen, and shaken at ambient temperature in a Parr hydrogenation apparatus, for 6 hours. The reaction mixture was then filtered through a 0.5 m Millipore filter to remove the Pd/C and the solvent removed in vacuo and was gel filtered through a Biogel P2 resin (25 g swollen with water). Acidification with HCl resulted in an orange brown solution, which was purged with nitrogen overnight. Removal of the solvent in vacuo gave the product as the hydrochloride salt which was a pale brown solid (3.98 g, contaminated with NaCl and glycolic acid, maximum theoretical amount of product 1.15 g). The product was used with no further purification.

EXAMPLE DD

Preparation of 4-isothiocyanatophenyl Methylenecarboxylate Terminated Third Generation Starburst Polyethyleneimine The product from Example CC (3.98 g) was dissolved in 15 ml of deionized water and an aliquot (2.5 ml) of this solution was diluted with 10 ml water. the pH of the solution was adjusted to 7 with sodium hydroxide. A pH stat (titrating with 1N NaOH) was used to maintain the pH and 200 µl thiophosgene was added. After 10 minutes the pH of the mixture was adjusted to 4 with hydrochloric acid. Water was removed on a rotary evaporator at reduced pressure (a small amount of n-butanol was added to prevent foaming). The residue was washed with methylene chloride and then dried. The crude product (0.95 g) a mixture of isothiocyanate (0.14 g) and salts was used without further purification.

EXAMPLE EE

Preparation of a Methylenecarboxylate-terminated Second Generation Starburst Polyamidoamine (Initiated from Ammonia)

The second generation starburst polyamidoamine (2.71 g, 2.6 mmol) and bromoacetic acid (4.39 g, 31.6 mmol) were dissolved in 30 ml of deionized water and the pH adjusted to 9.7 with 5N NaOH using a pH stat. The reaction was maintained at this pH for a half hour, and the temperature was slowly raised to 60° C. and was maintained at 60° C. for three hours at constant pH. The pH was raised to 10.3, and the reaction mixture remained under control of the pH stat at ambient temperatures overnight. The reaction mixture was refluxed for a further four hours prior to work up. Removal of the solvent, and azeotroping the final traces of water with methanol gave the product as a pale yellow powder (8.7 g, contaminated with sodium bromide). The $^{13}$C/NMR spectrum was consistent with the propose structure (with some contamination due to a small amount of defected material as a result of some monoalkylation).

EXAMPLE FF

Preparation of a Methylenecarboxylate Terminated Second Generation Starburst Polyethyleneimine (Initiated from Ammonia)

The second generation starburst polyethyleneimine (2.73 g, 6.7 mmol), from Example X, and bromoacetic acid (11.29 g 81 mmol) were dissolved in 30 ml of deionized water. The pH was slowly raised to pH 9.5 maintaining the temperature below 30° C. The temperature was raised slowly to 55° C., and the reaction pH maintained at 9.5 for 6 hours with the aid of a pH stat (titrating with 5N NaOH). The pH was raised to 10.2, and maintained at that pH overnight. Removal of the solvent on the rotary evaporator, and azeotroping the final traces of water using methanol, gave the product as a yellow powder (17.9 g, contaminated with sodium bromide). The $^{13}$C NMR spectrum was consistent with the proposed structure (with some contamination due to a small amount of defected material as a result of some monoalkylation).

EXAMPLE GG

Preparation of 3.5, 4.5, 5.5 and 6.5 Generation Starburst PAMAM

To a 10 weight percent methanolic solution of 2.46 g 3 generation PAMAM starburst was added 2.32 g of methyl acrylate. This mixture was allowed to sit at room temperature for 64 hours. After solvent and excess methyl acrylate removal, 4.82 g of product was recovered (105% of theoretical).

Preparation of Higher ½ Generation Starburst PAMAM's

Generations 4.5, 5.5 and 6.5 were prepared as described above with no significant differences in reactant concentrations, reactant mole ratios or reaction times.

EXAMPLE HH

Preparation of 4, 5 and 6 Generation Starburst PAMAM

To 2000 g of predistilled ethylenediamine was added 5.4 g of 4.5 generation starburst PAMAM as a 15 weight percent solution in methanol. This was allowed to sit at room temperature for 48 hours. The methanol and most of the excess ethylenediamine were removed by rotary evaporation under water aspirator vacuum at temperature less then 60° C. The total weight of product recovered was 8.07 g. Gas chromatography indicated that the product still contained 34 weight percent ethylenediamine at this point. A 5.94 g portion of this product was dissolved in 100 ml methanol and ultrafiltered to remove the residual ethylenediamine. The filtration was run using an Amicon TC1R thin channel recirculating separator equipped with an Amicon YM2 membrane. An in-line pressure relief valve was used to maintain 55 psig (380 kPa) pressure across the membrane. The 100 ml was first concentrated to 15 ml by forcing solvent flow exclusively through the membrane. After this initial concentration, the flow was converted to a constant volume retentate recycle mode for 18 hours. After this time, 60 ml of methanol was passed over the membrane to recover product still in the module and associated tubing. The product was stripped of solvent and 2.53 g of 5 generation starburst PAMAM was recovered. Analysis by gas chromatography indicated 0.3 percent residual ethylenediamine remained in the product.

Preparation of generation 4 and 6 proceeded as above with the only difference being the weight ratio of ethylenediamine to starting material. To prepare 4th generation this ratio was 200:1 and for 6th generation this ratio was 730:1.

EXAMPLE II

Modification of Polyamidoamine Dendrimers by Reaction with Epoxyoctane

To a solution of 0.50 g of sixth generation PAMAM in 5 ml of methanol was added 0.56 g of epoxyoctane. After 6 days at room temperature, the solvent was evaporated in vacuo to give 0.80 g of colorless oil. The material was soluble in chloroform, toluene or methanol, but not soluble in water. The $^{13}$C-NMR spectrum was in accord with a dendrimer with C-8 alkyl groups attached to its terminal amines.

EXAMPLE JJ

Modification of Polyamidoamine Dendrimers by Reaction with T-butyl Glycidyl Ether To a solution of 0.50g sixth generation PAMAM in 5 ml methanol was added 0.57 g of t-butyl glycidyl ether. After 6 days at room temperature, the solvent was evaporated in vacuo to give 1.0 g of colorless oil. The material was soluble in chloroform, toluene or methanol, but not soluble in water. The 13C-NMR spectrum was in accord with a dendrimer with 3-(t-butoxy)-1-propan-2-ol groups attached to its terminal amines.

EXAMPLE KK

Modification of Polyamidoamine Dendrimers by Reaction with Epoxyoctadecane

To a solution of 0.50 g of sixth generation PAMAM in 25 ml of methanol was added 1.1 g epoxyoctadecane. The solution was heated at reflux for 5 days. During the reflux time, a colorless viscous oil precipitated from the solution. The solvent was evaporated in vacuo to give 1.6 g of white foam. The material was soluble in chloroform or toluene, but not soluble in water or methanol. The $^{13}$C-NMR spectrum was in accord with a dendrimer with C-18 alkyl groups attached to its terminal amines.

EXAMPLE LL

Reaction of Starburst PEI with a Hydrophobic Epoxide

Into a flask equipped with a magnetic stirrer was added 0.397 g ($2\times10^{-4}$ moles) of fourth generation PEI (NH$_3$ core; MW 1,955) and 2.1 g ($9.6\times10^{-3}$ moles) of methyl 10,11-oxoundecanoate (MW 214.3); in 5 ml of methanol. The reaction mixture was stirred at room temperature for 1 day and then warmed at 80° C. for 8 hours to give a brown viscous syrup. Complete ring opening reaction to produce the carbomethoxy terminated, hydrophobic dendrimer was confirmed by NMR analysis and comparison to model systems.

The above hydrophobic dendrimer was converted into a water soluble form by simply combining an equivalent weight of this product with sodium hydroxide in water and heating for 30 to 60 minutes. A homogeneous solution, which showed no detectable carbomethoxy groups, was obtained. Addition of excesses of NaOH or NaCl caused the sodium carboxylate salt to become cloudy and phase out as an oil.

EXAMPLE 1

Incorporation of 2-(acetyloxy)benzoic acid (Aspirin) into Starburst Dendrimers

A widely accepted method for ascertaining whether a "probe molecule" is included in the interior of a micelle is to compare its carbon-13-spin lattice relaxation times ($T_1$) in a non-micellized versus micellized medium. A substantial decrease in $T_1$ for the micellized medium is indicative of "probe molecule" inclusion in the micelle. Since starburst dendrimers are "covalently fixed" analogs of micelles, this $T_1$ relaxation time technique was used to ascertain the degree/extent to which various pharmaceutical type molecules were associated with starburst polyamidoamines. In the following examples, $T_1$ values for (acetyloxy)benzoic acid (I) (aspirin) were determined in solvent (CDCl$_3$) and then compared to $T_1$ values in CDCl$_3$ at various [I:dendrimer] molar ratios.

Inclusion of aspirin (I) into various starburst polyamidoamine dendrimers as a function of generation.

Figure 4:
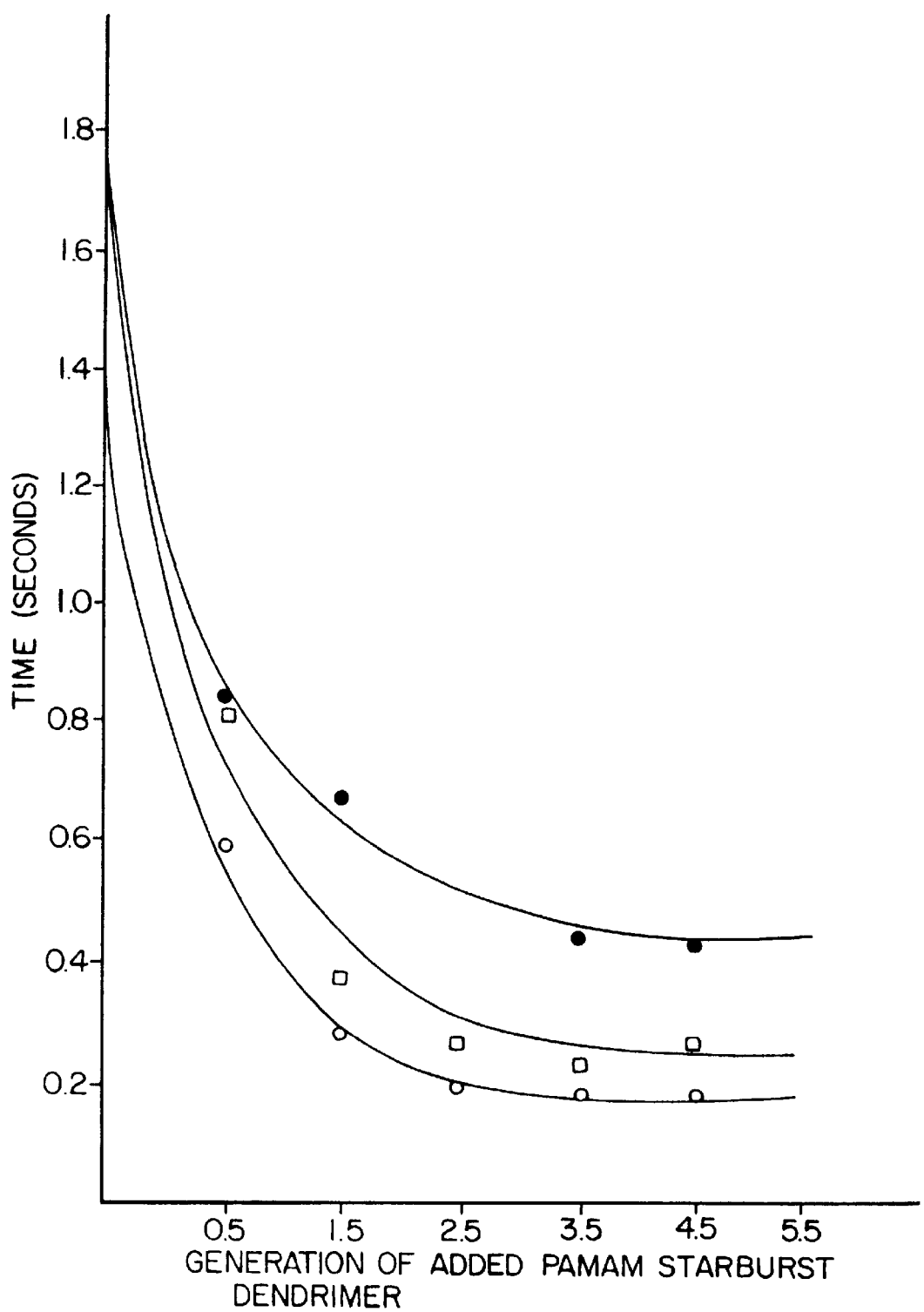
FIG. 4 shows carbon-13 spin lattice relaxation times ($T_1$) for aspirin incorporated into various dendrimer generations, Example 1.

Various half generation (ester terminated, initiated from NH$_3$) starburst polyamidoamine dendrimers (G=0.5→5.5) were combined with 2-(acetyloxy)benzoic acid in CDCl$_3$ to give acid:tertiary amine ratios of=1.0. A plot of $T_1$ values for 2-(acetyloxy)benzoic acid versus generation of starburst dendrimer added (see FIG. 4 where represent C-4, π represent C-6, and ○ represent C-5) shows that $T_1$ reaches a minimum over the generation range of 2.5→5.5 for carbons 4, 5 and 6 in 2-(acetyloxy)benzoic acid. This demonstrates interior association of 2-(acetyloxy)benzoic acid in the dendrimers (G=2.5→5.5) and further confirms that polyamidoamine dendrimers (Gen=2.5 or greater) can function as carrier molecules.

EXAMPLE 2

Release of Pseudoephedrine from Starburst Dendrimer-PAMAM

Pseudoephedrine (0.83 mg/ml) and starburst PAMAM dendrimer [1.0 mg/ml; G=6.5; terminal group (Z)=192 (methyl ester)] were dissolved in deionized distilled water and the pH of the donor phase was adjusted to 9.5, with sodium hydroxide solution, and stored at room temperature for about 12 hours. Solution of pseudoephedrine alone was treated in the same way (control). The drug dendrimer solution was stored at 40° C. for 8 hours after the first experiment and dynamic dialysis performed. Dialysis membrane used was a SpectraPor 7, MWCO 1,000, 28.6 mm in diameter in spectrum separation cells (half cell volume 5 and 10 ml, cell dimensions: 38 mm diameter for both the cells and the cell depth of 10 and 20 mm for 5 and 10 ml cells, respectively).

Samples were analyzed by a HPLC procedure developed for pseudoephrine conditions for which are as follows:

Column: uBondapak C-18

Mobile phase: pH 3.2 phosphate buffer plus acetonitrile (80:20)

Flow rate: 0.3 ml/min

Detection: UV at 210 nm

Retention time: 13.3 min

The dialysis membrane was washed with deionized water and was kept soaking in the receptor phase for at least 12 hours prior to use. The dialysis membrane was placed in between the donor and the receptor compartment was stirred with a small magnetic spin bar. Known volumes of donor and receptor solutions were introduced into the respective compartments and transfer of pseudoephedrine to the receptor compartment was followed as a function of time. To maintain sink conditions the entire receptor phase was removed periodically (every 30 minutes) and replaced with fresh receptor phase. The amount of pseudoephedrine was assayed in the sampled receptor phase. Experiments were conducted at room temperature (22° C.). The receptor phase was plain deionized distilled water.

Figure 5:
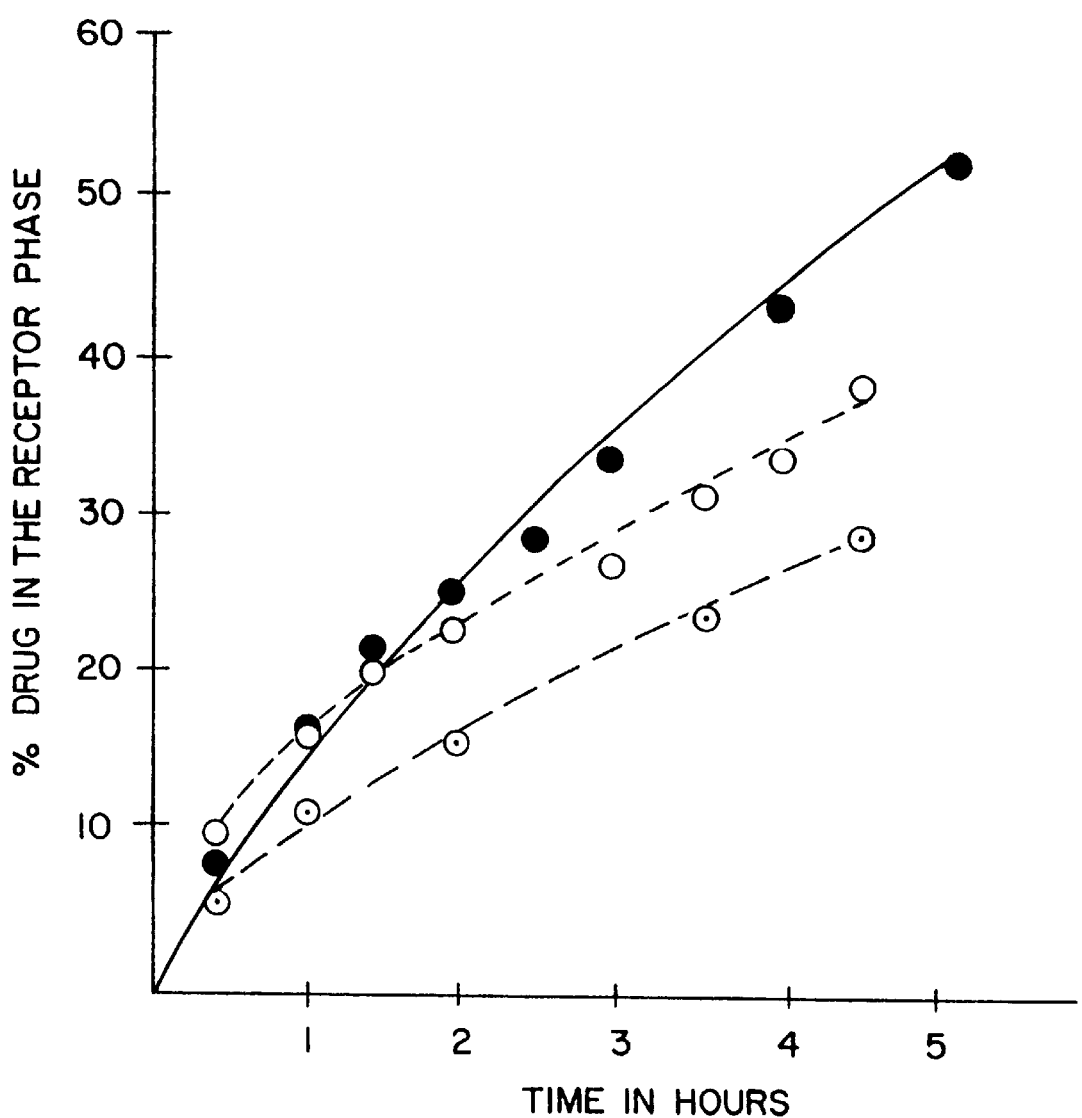
FIG. 5 shows the results of the dynamic analysis of Example 2.

The results of dynamic analysis are shown in FIG. 5. In FIG. 5, the ● represents pseudoephedrine only (control), the (I) represents pseudoephedrine plus the dendrimer, and the ○ represents pseudoephedrine plus the dendrimer at 40° C., 8 hours before dialysis. It is apparent that in presence of G 6.5 dendrimer in the donor compartment the rate of dialysis of pseudoephedrine is reduced. Storing the donor solution at 40° C., appears to further reduce the rate of dialysis.

The experiment was repeated at lower concentrations (the ratio of number of drug molecules to the number of terminal groups was kept the same). G 6.5 dendrimer 120 $\mu$/ml pseudoephedrine 100 $\mu$/ml (122 $\mu$/ml salt).

Figure 6:
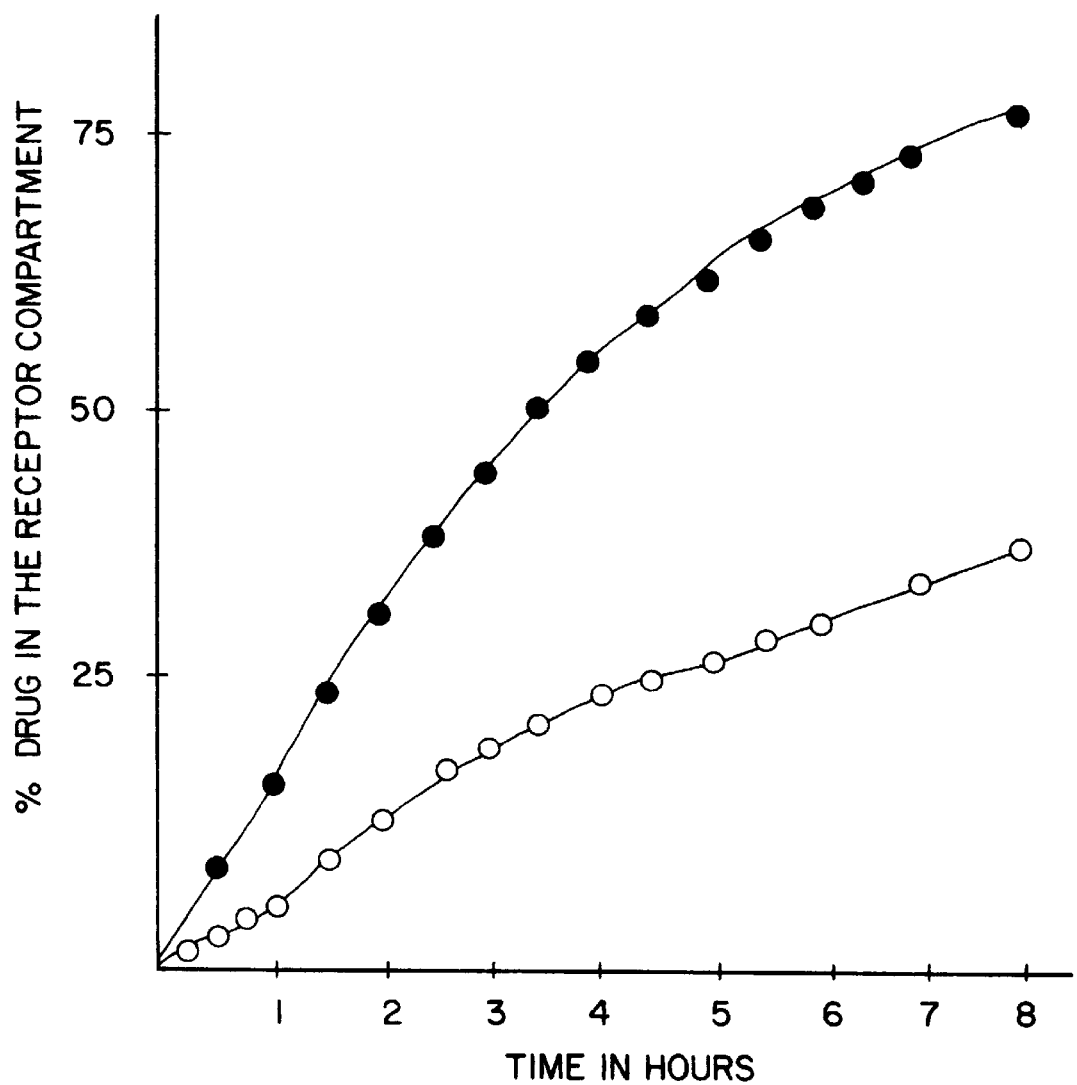
FIG. 6 shows the influence of generation 6.5 dendrimer on the dialysis rate of pseudoephedrine at pH 9.5 from Example 2.

Dynamic dialysis of pseudoephedrine (alone) at this lower concentration was almost identical to that at higher concentration. FIG. 6 summarizes the results of this experiment where ● represents pseudoephedrine only (control), and ○ represents pseudoephedrine plus dendrimer.

EXAMPLE 3

The procedure of Example 2 was repeated using the modifications given below.

Receptor phase: pH 7.4 phosphate buffer

Donor phase: pH 7.4 phosphate buffer plus drug and dendrimer in the following ratios:
1. G 6.5: Drug:: 1:192
2. G 5.5: Drug:: 1:96
3. G 4.5: Drug:: 1:48
4. G 6.5H: Drug:: 1:192
5. G 5.5H: Drug:: 1:96
6. G 4.5H: Drug:: 1:48

The above donor phase compositions plus pseudoephedrine alone were subjected to dynamic dialysis. The letter "H" after the dendrimer generation number stands for hydrolyzed dendrimer. Hydrolysis was accomplished by the procedure described in Examples M and N.

Figure 7:
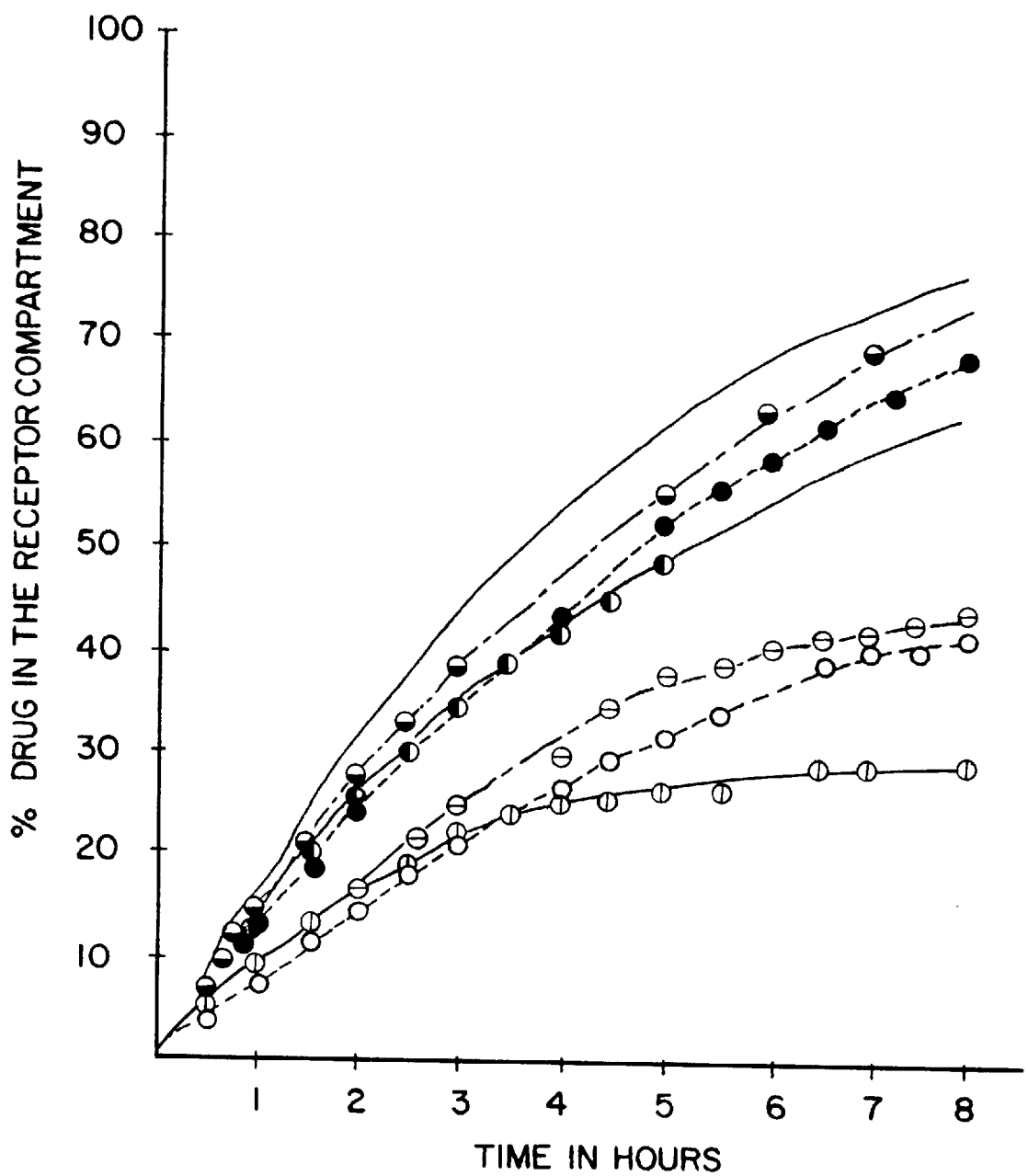
FIG. 7 shows the effect of dendrimer hydrolysis on the permeability of pseudoephedrine of Example 3.

The results of these experiments are summarized in FIG. 7 where the donor and receptor compartment contained pH 7.4 phosphate buffer. For pseduoephedrine alone (P) the mean curve of three experiments is plotted (shown by the solid line), and one typical run from the other experiments are shown. In FIG. 7, the following symbols represent the dendrimer of the indicated generation.

TABLE III

| Symbol | Dendrimer Generation |
| --- | --- |
| ○ | 5.5 |
| ● | 6.5 |
| ○ | 4.5 |

TABLE III-continued

| Symbol | Dendrimer Generation |
| --- | --- |
| ⊖ | 5.5H |
| ○ | 6.5H |
| ○ | 4.5H |

Pseudoephedrine appears not to associate with the dendrimer (hydrolized) at pH 7.4. Hydrolysis of the terminal functional groups into carboxylate form, has a dramatic effect on the dialysis rate (reduction). The generation number appears not to influence the dialysis rate.

EXAMPLE 4

Interaction Studies of Salicylic Acid with PAMAM Starburst Dendrimers

This example evaluated interaction characteristics of salicyclic acid with PAMAM starburst dendrimers. These dendrimers consisted of an ammonia initiated core with repeating units derived from N-(2-aminoethyl) acrylamide. Both full (amine terminated functions) and half (ester terminal groups) generation polymers were included in the studies. The ratio of salicyclic acid to starburst dendrimers utilized in the experiments resulted in approximately one salicyclic acid molecule to one terminal amine functional group for full generation polymers. In the half-generation polymer study, the same ratio was employed with adjustments made for the higher molecular weight polymer.

The experiments were conducted at room temperature using an equilibrium static cell dialysis methodology. Spectrum static dialysis cells (half cell volume, 10 ml) separated by SpectraPor 6 membranes (molecular weight cutoff=1000) were utilized for all experiments. Transport of salicyclic acid was monitored as a function of time by removing aliquots from appropriate cell compartments and assayed by HPLC analysis using a U.V. detector at 296 nm (Bondapak C-18 Column, eluting mobile phase of acetonitrile/0.1M phosphate buffer (pH 3.2) at a ratio of 20:80 (V/V), set at a flow rate of 30 ml/hour).

Figure 8:
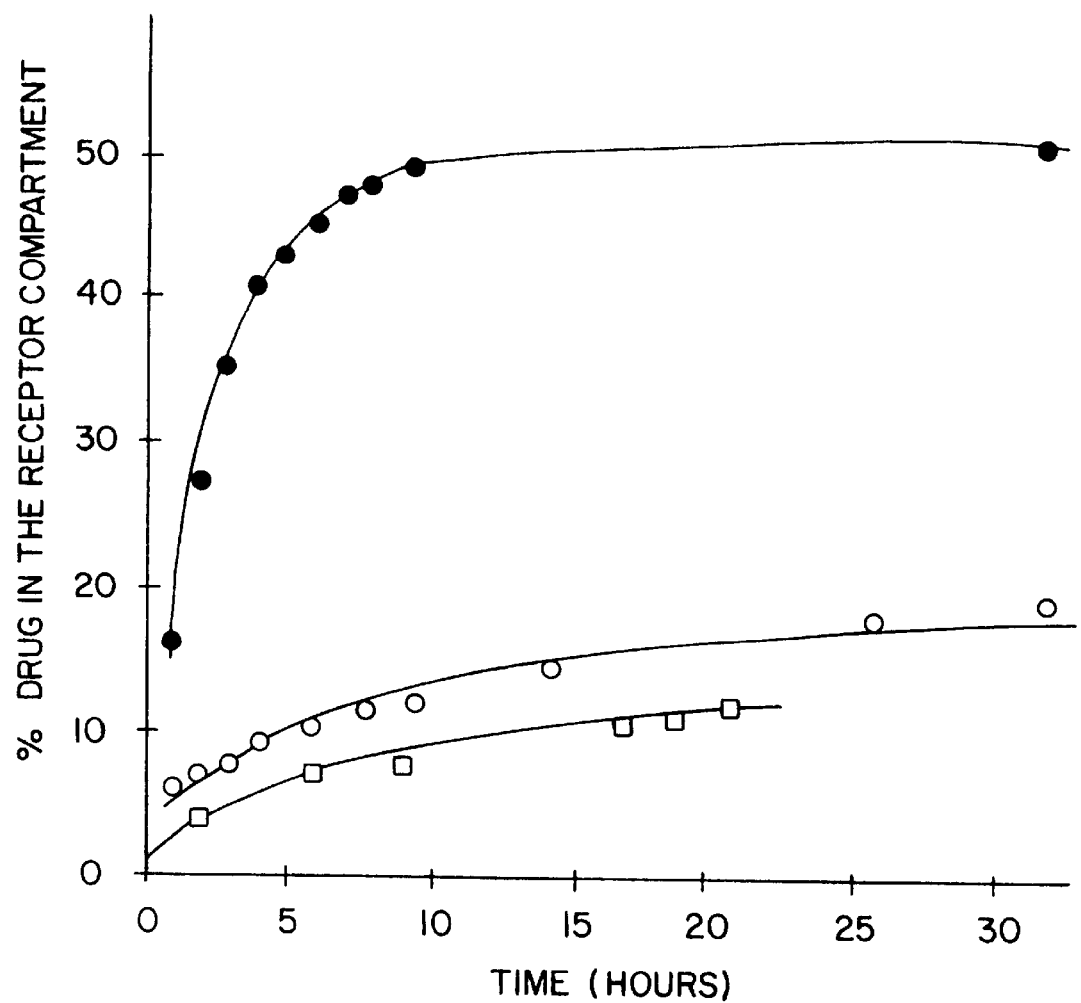

Ten ml of a solution containing 1 mg/ml salicyclic acid and 2.5 mg/ml starburst polymer (Gen 4.0) adjusted to pH 6.65 and 5.0 with HCL solution were placed in the donor compartment of the dialysis cell and an equal volume of purified water adjusted to the same pH's placed in the receptor compartment. Transport of salicyclic acid into the receptor compartment was monitored. The results are given in FIG. 8. In FIG. 8, the free acid is represented by ●, the acid plus generation 4.0 dendrimer, pH 6.65 is represented by ○, and the acid plus generation 4.0 dendrimer, pH 5.00 is represented by □.

Due to the lower percent ionization of the amine groups on the polymer at pH 6, a greater extend of interaction with salicylic may be expected at pH 5, resulting in less compound transported at the lower pH. The results given in FIG. 8 indicate a much lower percentage of salicyclic acid transported in the presence of polymer at both pH's studied compared to the salicyclic acid control study. It is also observed that more salicyclic acid is transported at pH 6.65 than at pH 5.0 as predicted. The data demonstrates an interaction of the starburst polymer with salicylic acid that can be controlled by pH. Sustained release characteristics are also implied by these data since the salicyclic acid levels in the presence of polymer continue to rise past the approximate 12-hour equilibrium point observed in the control study.

To further investigate the interaction characteristics of salicylic acid with starburst polymers (Gen=4.0) an experiment was designed at pH 8.0. The design of the study differed from that previously described in that only the salicylic acid solution (1 mg/ml), adjusted to pH 8.0, was placed in the donor compartment and the polymer solution (2.5 mg/ml) placed in the receptor compartment. Loss of salicylic acid from the donor compartment was monitored as previously described. The results of the experiment are given in FIG. 9. In FIG. 9, the free acid is represented by -●-, and the acid plus generation 4.0 dendrimer at pH 8.0 is represented by ---△---.

As indicated in FIG. 9, the equilibrium characteristics of salicylic acid in the donor compartment with starburst polymers in the receptor compartment differs from the salicylic acid control study. Based on the ionization characteristics of the molecules at pH 8, approximately 6–7% interaction is expected. The observed extent of interaction is indicated to be on the order of 4–5%. The lower association observed may be due to experimental variability or to an ionization constant of less than one.

This experiment indicates an uptake or removal of free salicylic acid from the continuous phase of the system by the polymer. This type of action could result in suppression of reactivity of molecules suggesting a possible chelating or molecular association type of property associated with the polymers.

The interaction characteristics of salicylic acid at pH 6.65 with a half generation starburst polymer (Gen=4.5) having ester terminated functional groups were evaluated. Salicylic acid (1 mg/ml) was combined with starburst polymer (Gen=4.5) 3.6 mg/ml at pH 6.65. Ten ml of the solution was placed in the donor compartment and transport from the donor compartment was monitored as previously described. The results are given in FIG. 10. In FIG. 10, the free acid is represented by -●-, and the acid plus polymer is represented by ---○---.

Under these experimental conditions no charge interaction is predicted to occur since the tertiary amine groups are non-ionized at pH 6.65. As is indicated in FIG. 10, the loss of salicylic acid in the presence of polymer (Gen 4.5) is virtually identical during the first 10 hours of dialysis to that of the salicylic acid control study.

The following observations are made from the data presented in this example:

(1) Full generation PAMAM starburst polymers function as a carrier for salicylic acid.
(2) Full generation PAMAM starburst polymers have sustained release functionality for salicylic acid.
(3) Salicylic acid carrier properties of full generation PAMAM starburst polymers can be controlled by pH.

EXAMPLE 5

Demonstration of Multiple Chelation of Iron by a Sodium Propionate Terminated Sixth Generation Starburst Polyamidoamine The sodium propionate terminated sixth generation polyamidoamine (initiated from ammonia) (97.1 mg, 2.45 mol.) was dissolved in 1.5 ml of deionized water. Addition of 0.5 ml of 0.5N HCl reduced the pH to 6.3. Ferric chloride was added (0.5 ml of 0.1.2M solution, 0.051 mmol) producing a light brown gelatinous precipitate. On heating at 60° C. for 0.5 hours, the gelatinous precipitate became soluble, resulting in a homogeneous orange solution. The solution was filtered through Biogel P2 acrylamide gel (10 g, twice) isolating the orange band (free of halide contamination). Removal of the solvent in vacuo gave the product as an orange film (30 mg). Analysis was consistent with chelation of approximately 20 moles of ferric ions per mole of starburst dendrimer.

TABLE IV

| Found | Theoretical | | |
|---|---|---|---|
| | $Na_4Fe_{20}H_{128}SB$ | $Na_5Fe_{20}H_{127}SB$ | $Na_6Fe_{20}H_{126}SB$ |
| Na 0.39, 0.24 (0.31 0.1%) | 0.25 | 0.31 | 0.38 |
| Fe 3.14, 3.11 (3.12 0.02%) | 3.05 | 3.05 | 3.04 |
| C 47.11 | 49.87 | 49.84 | 49.81 |
| H 7.33 | 7.31 | 7.30 | 7.29 |
| N 14.81 | 14.49 | 14.48 | 14.47 |
| O — | 25.03 | 25.02 | 25.01 |
| Mwt. | 36632.23 | 36654.21 | 36375.18 |

$SB = C_{1521}H_{2467}N_{379}O_{573}$

These results confirm chelation of 20±2 moles of ferric ions per mole of starburst dendrimer.

EXAMPLE 6

Preparation of a Product Containing more than One Rhodium Atom Per Starburst Polymer 2.5 Gen PAMAM (ester terminated, initiated from $NH_3$) (0.18 g, 0.087 mmole) and $RhCl_3.3H_2O$ (0.09 g, 0.3 mmole) were mixed in dimethylformamide (DMF) (15 ml) and heated for 4 hours at 70° C. The solution turned crimson and most of the rhodium was taken up. The unreacted rhodium was removed by filtration and the solvent removed on the rotary evaporator. The oil formed was chloroform soluble. This was washed with water and dried ($MgSO_4$) before removal of solvent to yield a red oil (0.18 g). The NMR spectrum was recorded in $CDCl_3$ only minor differences were noted between the chelated and unchelated starburst. Dilution of some of this $CDCl_{13}$ solution with ethanol followed by $NaBH_4$ addition resulted in rhodium precipitation. $RhCl_3.3H_2O$ is insoluble in chloroform and in chloroform starburst solution thus confirming chelation.

EXAMPLE 7

Preparation of a Product Containing Pd Chelated to a Starburst Polymer 3.5 Generation PAMAM (ester terminated, initiated from $NH_3$) (1.1 g, 0.24 mmole) was dissolved with stirring into acetonitrile (50 ml). Palladium chloride (0.24 g, 1.4 mmole) was added and the solution was heated at 70–75° C. (water bath) overnight. The $PdCl_2$ was taken up into the starburst. After removal of the solvent, the NMR in $CDCl_3$ confirmed that chelation had occurred. Dilution of the $CDCl_3$ solution with ethanol and addition of $NaBH_4$ resulted in precipitation of the palladium. The chelated product (1.23 g) was isolated as a brown oil.

EXAMPLE 8

Demonstration of Multiple Chelation of Yttrium by a Methylene Carboxylate Terminated Second Generation Starburst Polyethyleneimine by Trans Chelation from Yttrium Acetate The starburst polyethyleneimine methylene carboxylate terminated material (0.46 g 52.5 percent active, remainder sodium bromide, 0.18 mmol active starburst dendrimer), from Example FF, was dissolved in 4.5 ml of deuterium oxide. The resultant pH was 11.5–12. A solution of yttrium acetate was prepared by dissolving yttrium chloride (0.15 g, 0.5 mmol) and sodium acetate (0.41 g, 0.5 mmol) in 1.5 ml of deuterium oxide (2.9 moles of yttrium per mole of dendrimer). Aliquots of 0.5 ml of the yttrium acetate solution were added to the dendrimer solution and the $^{13}$C NMR spectra recorded at 75.5 MHz.

The $^{13}$C NMR spectrum of yttrium acetate shows two resonances, 184.7 ppm for the carboxyl carbon and 23.7 ppm for the methyl carbon, compared with 182.1 and 24.1 ppm for sodium acetate, and 177.7 and 20.7 ppm for acetic acid (Sadtler $^{13}$C NMR Standard Spectra). Monitoring the positions of these bands indicates degree of chelation with the starburst dendrimer. The most informative signal for the starburst dendrimer which is indicative of chelation is the α-CH$_2$ (of the methylene carboxylate group involved in chelation), which appears at 58.4 ppm in the unchelated dendrimer, and 63.8 ppm in the chelated dendrimer. Upon chelation with yttrium, the spin lattice relaxation times of the time α-CH$_2$ shortens as expected from 0.24±0.01 s to 0.14±0.01 s, indicative of chelation.

Following the addition of 0.5 ml of the yttrium acetate solution to the starburst dendrimer, all the yttrium appeared to be chelated by the dendrimer, confirmed by the signals for the acetate being that of sodium acetate. The same observation was noted for the addition of a second 0.5 ml aliquot of the yttrium acetate solution. Upon addition of the third aliquot of yttrium acetate, not all of the yttrium was observed to be taken up as the starburst chelate, the acetate carboxyl resonance was observed to shift to 183.8 ppm indicating that some of the yttrium was associated with the acetate. The integrated area of the chelated —CH$_2$ groups on the dendrimer increased, indicating that some of the third mole equivalent of yttrium added was indeed chelated with the dendrimer. These results indicate that the dendrimer can chelate from 2–3 yttrium ions per dendrimer molecule (Generation=2.0).

EXAMPLE 9

Demonstration of Multiple Chelation of Yttrium by a Methylene Carboxylate Terminated Second Generation Starburst Polyamidoamine by Trans Chelation from Yttrium Acetate The same experimental methods were used for this study as were used for Example 8. The starburst polyamidoamine methylene-carboxylate terminated material (0.40 g 62.5% active, remainder sodium bromide, 0.12 mmol.) was dissolved in 4–5 ml of deuterium oxide. The resultant pH was 11.5–12, which was lowered to 9.4 with 6N HCl prior to the experiment. A solution of yttrium acetate was prepared by dissolving yttrium chloride (0.1125 g, 0.37 mmol.) and sodium acetate (0.0915 g, 1.1 mmol.) in 1.5 ml of deuterium oxide, thus every 0.5 ml of solution contains one mole equivalent of metal.

The first two mole equivalents of yttrium acetate added were fully chelated by the starburst polyamidoamine. On addition of a third mole equivalent of yttrium, precipitation of the product occurred and as such no NMR data could be obtained. The signals which gave the most information about chelation by the starburst dendrimer were those of the two carbons adjacent to the chelating nitrogen. The chemical shifts of these carbons in the unchelated dendrimer occurred at 59.1 ppm for the α-CH$_2$, and 53.7 ppm for the first methylene carbon of the backbone. Upon chelation these two resonances were observed to shift downfield to 60.8 and 55.1 ppm respectively. The trans chelation shows that two metal ions can be readily chelated per dendrimer molecule, however upon chelation of some unknown fraction of a third mole equivalent, the product precipitates out of solution.

EXAMPLE 10

Demonstration of Multiple Chelation of $^{90}$Y by a Methylenecarboxylate Terminated Second Generation Starburst Polyethyleneimine Standard solution of yttrium chloride ($3\times10^{-2}$ M, spiked with non-carrier added $^{90}$Y) and methylenecarboxylate terminated second generation starburst polyethyleneimine ($6\times10^{-2}$ M) were prepared. These were reacted together at various metal:starburst ratios in HEPES buffer. The complex yield was determined by ion exchange chromatography using Sephadex G50 ion exchange beads, eluting with 10% NaCl:NH$_4$OH, 4:1 at pH 10. Noncomplexed metal is removed on the column, complexed metal elutes. Yields were obtained by comparing the radioactivity eluted with that on the column, using a well counter.

TABLE V

| Chelation of 2.5 Gen. PEI Acetate with $^{90}$Y | | | | | |
|---|---|---|---|---|---|
| Vol. Y + 3 | Vol. PEI | Vol HEPES | M:L Theor. | % Complex | M:L Act. |
| 5 | 30 | 370 | 0.1 | 110 | 0.1 |
| 10 | 30 | 360 | 0.2 | 101 | 0.2 |
| 20 | 30 | 350 | 0.4 | 95 | 0.4 |
| 30 | 35 | 340 | 0.5 | 97 | 0.5 |
| 30 | 30 | 340 | 0.5 | 102 | 0.5 |
| 60 | 30 | 310 | 1.0 | 99 | 1.0 |
| 120 | 30 | 250 | 2.0 | 100 | 2.0 |
| 180 | 30 | 180 | 3.0 | 94 | 2.8 |
| 250 | 30 | 120 | 4.1 | 80 | 3.3 |
| 300 | 20 | 80 | 7.5 | 44 | 3.3 |
| 300 | 20 | 70 | 5.0 | 40 | 2.0 |
| 300 | 20 | 70 | 5.0 | 41 | 2.0 |

All volumes in Table V are microliters

Within the accuracy of the experiments, these results indicate that the 2.5 Gen. starburst PEI acetate can chelate between 2 and 3 metals per dendrimer giving a soluble complex.

EXAMPLE 11

Conjugation of 4-isothiocyanatophenyl methylenecarboxylate Terminated Third Generation Starburst Polyethyleneimine with IgG Monoclonal Antibody.

The isothiocyanate, 10 mg (50 μmoles), from Example DD was dissolved in 500 μl of 3 mM indium chloride which had been spiked with radioactive indium-111 chloride and the pH was adjusted to 9 with 660 μl N NaOH. Aliquots of whole monoclonal antibody IgG CC-46 were then mixed with aliquots of the chelated starburst. The mixtures were shaken then left for 18 hours. The mixtures were then analyzed by HPLC (column Dupont Zorbax Biosphere GF-250; eluent 0.25 M sodium acetate, pH 6) and a UV detector at 254 nm and a radioactivty detector. Results are shown in Table VI.

TABLE VI

| | Starburst-IgG Conjugates | | | |
|---|---|---|---|---|
| | 1 | 2 | 3 | 4 |
| IgG solution (μl) | 20 | 20 | 20 | 20 |
| Chelated Starburst solution (μl) | 5 | 20 | 50 | 100 |
| % Radioactivity on IgG | 6 | 5 | 5 | 3 |
| % IgG conjugated | 2 | 7 | 17 | 22 |

EXAMPLE 12

Conjugation of 4-isothiocyanatophenyl methylenecarboxylate Terminated Third Generation Starburst Polyethyleneimine with IgG Monoclonal Antibody The isothiocyanate from Example DD, 4 mg (20 μmoles) was mixed with 200 μl of 3 mM indium chloride (60 μmoles). A 20 μl aliquot of the solution was then spiked with radioactive indium-111 chloride and the pH adjusted to 9 by the addition of 30 μl 1 N NaOH and 10 μl of 0.1 N HCL. The indium chelate was mixed with 150 μl of CC-49 whole antibody IgG, 10 mg/ml in 50 mM HEPES bufffer at pH 9.5. After 18 hours at room temperature the antibody was recovered by preparative HPLC (column Dupont Zorbax Biosphere GF 250; eluent 0.25 m sodium acetate, pH 6); and a UV detector at 254 nm and a radioactivity detector. The recovered antibody was concentrated on an Amicon membrane and exchanged into PBS buffer (phosphate buffered saline pH 7.4 which contains 0.12M NaCl, 2.7 mM KCl and 10.0 mM phosphate) at pH 7.4. The recovered antibody had specific activity of approximately 0.5 μci/100 μg.

EXAMPLE 13

In vivo Localization of $^{111}$In Labeled Starburst Antibody Conjugate

The usefulness of the labeled starburst antibody conjugate prepared in Example 12 was demonstrated by measuring the uptake of the material by a human tumor xenograft in an athymic mouse. Female athymic mice were innoculated subcutaneously with the human colon carcinoma cell line, L-174T (approximately 4×10$^6$ cells/animal). Approximately two weeks after innoculation,each animal was injected via the tail vein. The mice were sacrificed after 17 and 48 hours (five animals at each time point), the tumor and selected tissues were excised and weighed, and radioactivity was measured in a gamma counter. After 17 hours 13.5 percent of the injected dose per gram of tissue had localized at the tumor. After 48 hours 21.6 percent of the injected dose per gram of tissue had localized at the tumor.

EXAMPLE 14

Attachment of Herbicidal Molecules (2,4-D) to the Surface of Starburst Dendrimers Third generation PAMAM (initiator core=NH$_3$) (2.0 g, 0.8 mmole) was dissolved in H$_2$O (10 ml) and combined with toluene (20 ml). The two-phase system was then stirred and cooled with an ice bath at which time the acid chloride of 2,4-D [2,4-dichlorophenoxy)-acetic acid] (2.4 g, 12 equiv) dissolved in toluene (10 ml) was added dropwise over 30 minutes. When the addition was nearly complete, NaOH (0.5 g, 12.5 mmole, 50% w/w solution) was added and the solution stirred for an additional two hours. The reaction mixture was then evaporated to dryness and the resulting solid residue repeatedly taken up in CHCl$_3$/MeOH (1:1) and filtered. The tan solid was not totally soluble in CHCl$_3$ and appeared to be insoluble in water; however, the addition of acetone facilitated dissolution. The tan solid was stirred in CHCl$_3$ for 24 hours and the solution filtered (a sticky tan solid was obtained). After drying over MgSO$_4$, the filtrate was concentrated to give a viscous orange oil which solidified on standing. The $^{13}$C NMR indicated partial amidation at the surface by 2,4-D and is consistent with the association of the 2,4-D to starburst polymer.

EXAMPLE 15

Inclusion of 2,4-dichlorophenoxyacetic acid (2,4-D) into Starburst Dendrimers

A widely accepted method for ascertaining whether a "probe molecule" is included in the interior of a micelle is to compare its carbon-13-spin lattice relaxation times ($T_1$) in a non-micellized versus micellized medium. A substantial decrease in $T_1$ for the micellized medium is indicative of "probe molecule" inclusion in the micelle. Since starburst dendrimers are "covalently fixed" analogs of micelles, this $T_1$ relaxation time technique was used to ascertain the degree/extent to which various herbicide type molecules were associated with starburst polyamidoamines. In the following examples, $T_1$ values for 2,4-dichlorophenoxyacetic acid (I) (2,4-D) were determined in solvent (CDCl$_3$) and then compared to $T_1$ values in CDCl$_3$ at various [I:dendrimer] molar ratios.

Inclusion of 2,4-D into various starburst polyamidoamine dendrimers as a function of generation.

Various half generation (ester terminated, initiated off NH$_3$) starburst polyamidoamine dendrimers (Generation (Gen)=0.5, 1.5, 2.5, 3.5, 4.5 and 5.5) were combined with 2,4-dichlorophenoxyacetic acid (I) in CDCl$_3$ to give an acid:tertiary amine ratio of 1:3.5 and molar ratios of acid:dendrimer of 1:86 as shown in Table VII. The relaxation times ($T_1$) obtained for the various carbon atoms in 2,4-dichlorophenoxyacetic acid and a generation=3.5 starburst PAMAM dendrimers are shown in Table VIII, both for 1:1 acid/amine ratios and for saturated solutions of 2,4-D.

TABLE VII

| Gen | (A) Acid/Amine | (B) Acid/Amine | (C) Acid/Total Nitrogen | (D) Molar Ratio (Acid/Starburst) |
|---|---|---|---|---|
| 0.5 | T | — | 1 | 1 |
| 1.5 | 1 | 1.33 | 0.57 | 6 |
| 2.5 | 1 (3.5)* | 1.11 (3.8)* | 0.53 (1.8)* | 9 (34)* |
| 3.5 | 1 (3.0)* | 1.05 (3.2)* | 0.51 (1.6)* | 20 (67)* |
| 4.5 | 1 | 1.02 | 0.51 | 42 |
| 5.5 | 1 | 1.01 | 0.50 | 86 |

*represents examples of 2,4-D inclusion into the interior of the dendrimer in amounts greater than stoichiometric.

TABLE VIII $T_1$'s for 2,4-D/G = 3.5 PAMAM Starburst
Inclusion complex: Concentration Effects

| | (A) 1:1 Acid/Amine | | (B) Saturated with 2,4-D | |
|---|---|---|---|---|
| Carbon | $T_1$ | $^{13}C**$ | $T_1$ | $^{13}C**$ |
| 1 | 3.19 ± .12 | (152.73) | 3.08 ± .09 | (152.30) |
| 3 | 0.34 ± .01 | (128.64) | 0.29 ± .01 | (129.62) |
| 5 | 0.38 ± .01 | (127.41) | 0.32 ± .01 | (127.34) |
| 2 | 3.28 ± .08 | (125.79 | 2.72 ± .68 | (125.99) |
| 4 | 4.58 ± .16 | (123.27) | 3.95 ± .07 | (123.16) |
| 6 | 0.31 ± .01 | (114.66) | 0.28 ± .01 | (114.48) |
| $CH_2$ | 0.16 ± .01 | (67.29) | 0.146 ± .003 | (66.79) |
| C=O | 1.24 ± .07 | (170.12) | | |

**represents $^{13}C$ chemical Shifts referenced to chloroform at 76.9 ppm.

These data show that larger than stoichiometric amounts of 2,4-dichlorophenoxyacetic acid (i.e., [(I):Gen=3.5 dendrimer)]=67 can be used without increasing the $T_1$ in any case in the saturated state (see Columns (A) and (B) in Table VIII). In fact, the relaxation times $T_1$ (Column (B)) are decreased slightly, thus indicating that larger than stoichiometric amounts of 2,4-dichloro-phenoxyacetic acid can be included into the interior of the dendrimer. For example, a molar ratio of [(I):Gen=2.5 dendrimer]=34 whereas [(I):Gen=3.5 dendrimer]=67, (see Column D in Table VII).

FIG. 11 is a plot of $T_1$ values for carbons-3, 5 and 6 in 2,4-dichlorophenoxyacetic acid as a function of dendrimer generation (i.e., 0.5→5.5). A minimum in $T_1$ is reached in all cases for generation 2.5→5.5, thus indicating incorporation in that dendrimer generation range is occurring. FIG. 11 also includes $T_1$ values for 2,4-D in the presence of triethylamine [N(Et)$_3$] and N(Et)$_3$+N-methylacetamide. It can be seen that these values are much larger than for dendrimers G=1.5 →5.5, thus further supporting molecular incorporation into the dendrimer molecule.

EXAMPLE 16

Preparation of a Product Containing Fluorescein with a Starburst Polymer

A sample of 5-carboxyfluorescein (0.996 g) and starburst polyethyleneimine (Gen=2.0; amine terminated, initiated off NH$_3$) (0.202 g) were mixed in 10 ml of methylene chloride and 5 ml of methanol and allowed to reflux for 10 minutes. Upon filtering, an insoluble red powder (0.37 g) was obtained (mostly unreacted 5-carboxy fluorescein). From the filterate was isolated 0.4 g of a brilliant-red solid which exhibited a softening point of 98–103° C. and foamed to a brilliant red melt at 175–180° C.; NMR spectra (D$_2$O) of this product were consistent with dendrimer having fluorescein bound to the surface.

EXAMPLE 17

In a Procedure Similar to that Described in Example 16, starburst polyethyleneimine (Gen=2.0; amine terminated, initiated off NH$_3$) was reacted with fluorescein isothiocyanate to give a brilliant-red iridescent solid which was suitable for use as a fluorescent labelling reagent.

EXAMPLE 18

Encapsulation of R(+)-Limonene in Polyamidoamine Starburst Dendrimers

A 5–50 weight percent solids solution in methanol of starburst—PAMAM dendrimer (M.W. about 175,000; generation=9.0) is added dropwise to R(+) limonene in methanol until saturated. The solution is stirred at room temperature (about 25° C.) for several hours and then devolatized on a Büchi rotovap at room temperature to give a solid product. Warming at temperatures greater than 80° C. gives solvent insoluble products which retain substantial amounts of R(+) limonene in an encapsulated form. These products are excellent prototypes for slow release of (R+)-limonene as a fragrance and deodorizer product.

EXAMPLE 19

Encapsulation of Heavy Metal Salts in Polyamidoamine Starburst Dendrimers

A 5–50 weight percent solids solution in water of starburst PAMAM dendrimer (M.W. about 350,000; generation=10.0) is stirred as a saturated solution of lead acetate [Pb(C$_2$H$_3$O$_2$)$_2$] is added dropwise. The solution is stirred at room temperature (about 25° C.) for several hours and then devolatilized on a Büchi rotovap to give solid products. Scanning transmission electron-micrograph of these products showed that these heavy metal salts are encapsulated in the interior of the dendrimers. These films containing heavy metal salts are useful as shields for absorbing electromagnetic radiation.

EXAMPLE 20

Encapsulation of Fluorescein (Water Soluble) Dye in Polyamidoamine Starburst Dendrimers A 5–50 weight percent solids solution (H$_2$O /CH$_3$OH) of starburst—PAMAM dendrimer (M.W. about 175,000; generation=9.0) is stirred as fluorescein, disodium salt (Acid Yellow 73, Cl. 45350; Uranine; available from Aldrich (Chemical Co., Milwaukee, Wis.) is added until saturated. The solution is stirred at room temperature (about 25° C.) for several hours and then devolatilized at room temperature to give a colored solid product. These dye encapsulated dendrimers are excellent reference probes for calibrating ultrafiltration membranes.

EXAMPLE 21

Preparation of Dendrimers with Terminal Fluorescent Groups

A. Reaction of Amine Terminated Dendrimer with N-Dansyl Aziridine

A sample (1.5 g, 1.6×10$^{-3}$ mole) of starburst polyethyleneimine (PEI), G=3.0, terminal groups (Z)=12, M.W.=920) is dissolved in 20 ml of methanol. The solution is stirred and 0.884 g (3.84×10$^{-2}$ mole) of a solution of N-dansyl aziridine (ICN Biomedicals, Costa Mesa, Calif.) is added dropwise over a period of 20 minutes. The reaction mixture is allowed to stir at room temperature overnight. Removal of solvent under vacuum gives a solid product. NMR and infrared analysis indicate that the product possessed covalently bonded dansyl groups on the surface of the dendrimer.

B. Reaction of Amine Terminated Dendrimers with Dansyl Chloride

A solution of starburst polyamidoamine (1.0 g, 1.9×10$^{-4}$ mole) (initiated from ammonia, G=4.0, terminal groups (Z)=24, M.W.=5,147) in 30 ml of water is stirred in a 3-neck flask with 80 ml of toluene while a solution of dansyl chloride (1.23 g, 4.5×10$^{-3}$ mole) (5-dimethyl-amino-1-naphthalenesulfonyl chloride, from Aldrich Chemical Co., Milwaukee Wis.) in 40 ml of toluene is added dropwise while cooling with ice. Concurrently, a solution of 10% NaOH (13.3 mole, 10% excess) is added to the reaction mixture to give an oily ball. The product is washed with water, dissolved in methanol, and precipitated with diethyl ether to give a solid product. NMR and infrared analyses are consistent with covalently bonded dansyl groups on the dendrimer surface.

EXAMPLE 22

Preparation of Manganese PAMAM Dense Star Polymer

Following the procedure set forth in Example 1 of U.S. Pat. No. 4,587,329, a third generation ester-terminated polyamidoamine dense star polymer is prepared. The ester moieties are hydrolyzed to sodium salt form by dissolving the dense star polymer in 0.1 N NaOH. A 131-mg (0.496 mmol) portion of the resulting crude sodium salt of the dense star polymer is dissolved in water (1 ml, pH 11.4) and neutralized to a pH of 7.0 by adding 0.5 M HCl. A 26-mg (2 equiv) portion of $MnCl_2.4H_2O$ is added to the neutralized solution and the solution is heated at 55 C. for 2 days. The resultant light yellow solution is purified using a Bio-Gell P2 column (15.0 g, 150 mm length×25 mm diameter) eluting with water, and isolating the colored band. The product was confirmed to be chloride free (e.g. NaCl, $MgCl_2$) by silver nitrate test. The eluate is stripped to dryness to produce a clear gel which is dried under high vacuum to yield 45 mg of the desired dense star polymer complex which is determined to have the following elemental constituency, $[NaMn_2H_7][C_{69}H_{105}N_{19}O_{33}]$, Calculated: Na, 1.23; Mn, 5.88; C, 44.35; H, 5.66; N, 14.24;

Found: Na, 1.42; Mn, 4.80; C, 43.33; H, 7.91; N, 14.72.

Following a similiar procedure using a seventh generation sodium carboxylate-terminated polyamidoamine dense star polymer, an additional manganese dense star polymer complexis prepared which is determined to have the following elemental constituency, $[Na_{30}H_{354}]$ $[Mn_{10}C_{3057}H_{4965}N_{763}O_{1149}]$, Calculated: Mn, 0.759; C, 50.72; H, 7.41; N, 14.76;

Found: Mn, 0.72; C, 46.34; H, 7.91; N, 14.72.

The relaxivities for the foregoing complexes are measured in water and the results are reported in Table IX. For the purposes of comparison, the relaxivities of complexes of manganese with two known complexing agents are calculated from the corresponding relaxation times measured by nuclear magnetic resonance. The results are reported in Table IX.

TABLE IX

| COMPOUND | RELAXIVITY* | |
| --- | --- | --- |
|  | $R_1$ | $R_2$ |
| $MnCl_2$ | 5.2 | >20 |
| MnEDTA | 2.9 | — |
| MnDTPA | 1.3 | — |
| $Mn_2$[PAMAM-A(2.5G)] | 3.63 ± 0.02 | 16.35 ± 0.78 |

*$(mM.sec)^{-1}$, 37° C., 90 MHz. Values per metal atom.

EXAMPLE 23

Following the procedure of Example 22, dense star polymer complexes of iron are prepared. In one embodiment, the sodium salt of the acid form of a sixth generation polyamidoamine is prepared by dissolving the ester form of the polyamidoamine made in accordance with the excess reactant method of U.S. Pat. No. 4,587,329 in N NaOH. The sodium salt (97 mg, $2.4 \times 10^{-3}$ mmol) is then dissolved in 2 ml of water and the solution (pH of 11.3) is neutralized to a pH of 7 with 0.5 M HCl. To this neutralized solution is added an aqueous solution of $FeCl_3$ (0.102 M, pH 1.4, 0.5 ml, 0.051 mmol, 21.6 equiv). The resulting deep orange solution (pH 4.9) is heated at 55° C. for 23 hr. The solution is cooled to ambient temperature and filtered by gel filtration chromatography (Biogel P2 column, 175×25 mm). The orange eluate is stripped to dryness under vacuum at 50° C. to yield 45 mg of an orange solid having the following molecular formula: $[Na_5H_{127}][Fe_{20}(PAMAM-P(6.5G))]$ wherein PAMAM-P represents the dense star polyamidoamine in the propionate terminated form. This orange solid is determined to be a complex of iron and the polyamidoamine dense star polymer represented by the formula $Na_5H_{127}Fe_{20}$ $(C_{1521}H_{2469}N_{379}O_{573})$, Calculated: Na, 0.31; Fe, 3.05; C, 49.84; H, 7.30; N, 14.48;

Found: Na, 0.31; Fe, 3.12; C, 47.11; H, 7.33; N, 14.81.

Following the above procedure, similar complexes of iron and acetate-terminated polyamidoamine dense star polymers or acetate-terminated polyethylenimines dense star polymers having from 2 to 6 generations are prepared. The relaxation times for these complexes are measured using nuclear magnetic resonance and the corresponding relaxivities are calculated and reported in Table X.

TABLE X

| COMPOUND | RELAXIVITY* | |
| --- | --- | --- |
|  | $R_1$ | $R_2$ |
| $FeCl_3$ | 8.4 ± 0.1 | — |
| FeEDTA | 1.7 |  |
| FeDTPA | 0.73 | 0.85 |
| FeEHPG | 0.95 | 1.1 |
| $Fe_2$[PEI-A(2.5G)] | 0.40 ± 0.02 | 0.88 ± 0.03 |
| $Fe_2$[PAMAM-A(2.5G)] | 0.77 ± 0.01 |  |
| $Fe_2$[PAMAM-P(2.5G)] | 0.135 ± 0.004 | 0.42 ± 0.02 |
| $Fe_4$[PAMAM-P(4.5G)] | 0.038 ± 0.006 | 1.01 ± 0.05 |
| $Fe_{20}$[PAMAM-P(6.5G)] | 0.047 ± 0.007 | 0.50 ± 0.07 |
| $Fe_{50-60}$[PAMAM-P(7.5G)] | about 0.3** | about 62** |
| {SPEI-[DTPA][Fe(DTPA)]$_2$} | 1.094 ± 0.050 | 1.70 ± 0.02 |

*$(mM.sec)^{-1}$, 37° C., 90 MHz. Values per metal atom.
**Values per complex.

EXAMPLE 24

Using the method of Example 22 complexes of gadolinium and the polyamidoamine and polyethylenimine dense star polymers described in Example 23 are prepared and their relaxation times are measured and relaxivities calculated with the result being shown in Table XI. As an illustration of the preparation of the gadolinium complex, 0.40 g (0.16 mmol) of the sodium acetate form of a polyethylenimine dense star polymer (second generation) prepared as in Example 6 of U.S. Pat. No. 4,587,329 and followed by reaction with an excess of bromoacetic acid at pH=9, 40° C., is dissolved in 5 ml of water. The pH of the resulting solution is lowered to 9.2 with 0.5 N HCl and 3.2 ml of an aqueous solution of $GdCl_3$ (0.31 mmol) is added. The pH of the resulting solution is increased from 4.1 to 8.3 with 1 N NaOH and the solution is allowed to stand for 24 hrs. The volatiles are then removed from the solution invacuo and the residue twice chromatographed in chelex resin. The recovered light yellow solid was found to have an atomic ratio of Gd to N of 2:1.

Found (%): C, 14.5; H, 2.1; N, 3.6; Gd, 7.9; Br, 28.7.

Following the above procedure, similar complexes of gadolinium and acetate-terminated polyamidoamine dense star polymers or acetate-terminated polyethylenimines dense star polymers having from 2 to 6 generations are prepared. The relaxation times for these complexes are measured using nuclear magnetic resonance and the corresponding relaxivities are calculated and reported in Table XI.

TABLE XI

| COMPOUND | RELAXIVITY* $R_1$ |
|---|---|
| $Gd(NO_3)_3$ | 8.6 ± 0.3 |
| $GdCl_3$ | 8.7 ± 0.1 |
| $GdCl_3$(0.15M saline) | 10.43 ± 0.36 |
| GdEDTA | 6.5 |
| GdDTPA | 3.9 |
| GdDOTA | about 4 |
| Gd(PAMAM-A) | 9.90 ± 0.43 |
| $Gd_2$(PAMA,M-A) | 13.00 ± 0.33 |
| Gd(PEI-A) | 8.85 ± 0.19 |
| $Gd_2$(PEI-A) | 15.35 ± 0.17 |
| $Gd_2$(PEI-A) + 3PEI-A | 8.0 ± 0.19 |
| Gd(DTPMP) | 10.8 ± 0.4 |
| $Gd_2$(PEI-A) + 2EDTA | about 6 |

(mM-sec)$^{-1}$, 37° C., 90 MHz. Values per metal atom.

EXAMPLE 25

Preparation of Polyamidoamine Starburst Conjugate with Bradykinin C

Bradykinin Potentiator C, 4.7 mg (Sigma Chemical Company), was taken up in 90 μL of N-methylpyrrolidinone (NMP) containing 7.1 mg/mL N-hydroxybenzotriazole (HOBT) and mixed with 33 μL of a freshly prepared solution of dicyclohexylcarbodiimide (DCC) (28 mg/ml NMP). After four hours at room temperature, 60 μL of fifth generation (5G) PAMAM in NMP (13.4 mg/ml) was added to the Bradykinin mixture. After 72 hours at room temperature, 1.5 ml of 17 mM acetic acid was added. The mixture was centrifuged and the solution decanted from the solid and the solid then washed with 1.5 mL of dilute acetic acid. The solution and washings were combined and filtered through a 25 mm PTFE 0.45μ syringe filter. Unreacted peptide, HOBT and solvent were separated from the conjugate by ultrafiltration using two Centricon-10 Microconcentrators. The conjugate was washed with 2 mL of 17 mM acetic acid, then 2 ml PBS buffer. The conjugate was recovered in 450 μL of retentate and diluted to 750 μL with fresh PBS buffer.

Four aliquots of the conjugate were hydrolyzed with concentrated HCl at 115° C. for 20 hours and analyzed for glutamic acid. The glutamic acid was quantified as the o-phthalaldehyde/2-mercaptoethanol derivative using reverse phase HPLC with a florescence detector (column: Whatman Partisil 5CCS/C8 (10 cm); Gilson Spectra/Glo detector; tyrosine as internal standard; eluent 50 mM sodium acetate and methanol; gradient: 12% to 30% methanol in 5 min., held for 1 min. at 30%, then increased to 80% methanol over 14 min. and held at 80% for 5 min.). The o-phthalaldehyde derivative was prepared by mixing 25 μL of the amino acid solution with 50 μL fluoraldehyde™ o-phthalaldehyde reagent solution (Pierce), mixing for one minute and then diluting with 0.05 ml of PBS buffer (phosphate buffered saline; 120 millimolar sodium chloride, 2.7 millimolar potassium chloride, 10 millimolar phosphate buffer salts, pH 7.4). For a 25 μL aliquot of the conjugate, 58 nmoles of glutamic acids were found. This corresponds to 1.74 μmoles Bradykinin C on the conjugate.

EXAMPLE 26

Preparation of Polyamidoamine Starburst Conjugate with BOCPheLeuPheLeuPhe

N-tert-butoxy-carbonyl-L-Phenylalanyl-D-Leucyl-L-Phenylalanyl-D-Leucyl-L-Phenylalanine (BOCPheLeuPheLeuPhe), 4.1 mg (Sigma Chemical Company), was taken up in 100 μL NMP which contained 7.1 mg/mL HOBT and mixed with 30 μL of a freshly prepared solution of DCC (36 mg/mL) in NMP. After 90 minutes at room temperature, 60 μL of a solution of 5G PAMAM in NMP (13.4 mg/mL) was added. After 72 hours at room temperature, the conjugate was isolated following the procedure in Example 24. The conjugate was recovered in 750 μL of retentate.

Four aliquots of the conjugate were hydrolyzed with concentrated HCl at 115° C. for 20 hours and analyzed for phenylalanine. The phenylalanine was quantified as the o-phthalaldehyde/2-mercaptoethanol derivative using reverse phase HPLC with a fluorescence detector (HPLC conditions as Example 24 except the eluent gradient was 12% to 80% methanol over 20 min. and then held at 80% for 5 min.). The o-phthalaldehyde derivative was prepared as given in Example 24. For a 25 μL aliquot of the conjugate, 26 nmoles phenylalanine were found. This corresponds to 0.26 μmoles BOCPheLeuPheLeuPhe on the conjugate.

EXAMPLE 27

To a methanol solution of 1,4,7-tris-(carbomethoxymethyl)-1,4,7,10-tetraazacyclododecane (DO3A methyl ester) is added 1.0 equivalent of freshly prepared anhydrous sodium methoxide and the solution is allowed to stir for several hours. To this solution is added one equivalent of 10,11-epoxyundecanoic acid and the solution is brought to reflux overnight. The solvent is removed in vacuo to give a crude hydroxyethylated product, 1,4,7-tris-(carbomethoxymethyl)-10-[2'-hydroxy-10'-carboxy(decyl)]-1,4,7,10-tetraazacyclododecane. Two to five equivalents of this product are dissolved in dimethylformamide (DMF) and corresponding equivalents of dicyclohexylcarbodiimide (DCC) and N-hydroxysuccinimide are added with stirring overnight. To this solution is added one equivalent of generation 2 PAMAM and stirring is continued another 24 hours. The corresponding DO3A methyl ester conjugate is selectively hydrolyzed by treatment with aqueous sodium hydroxide in methanol. Treatment of the DO3A conjugate with excess Gadolinium(III) acetate ($Gd(OAc)_3$) (buffered to pH=6) followed by incubation with excess diethylenetriaminepentaacetic acid (DTPA) and purification of the conjugate using preparative reverse phase HPLC gives a hydroxyethyl DO3A PAMAM starburst conjugate product which contains two to five equivalents of gadolinium which can not be removed by further challenges with excess DTPA.

EXAMPLE 28

To an aqueous solution of generation 2 PAMAM, which is buffered to pH=9.0, is added two to five equivalents of 1-[1-carboxy-3(4'-isothiocyanato-phenyl)propyl]-4,7,10-tris(carboxymethyl) -1,4,7,10-tetraazacyclododecane prepared by the method of described in EP published application 0353450, published Feb. 7, 1990. The solution is stirred overnight at room temperature. Treatment of the solution with excess $Gd(OAc)_3$ at pH=6.0 results in the formation of a thiourea linked DOTA PAMAM starburst conjugate which contains two to five equivalents of inertly bound gadolinium which can not be removed with a DTPA challenge.

We claim:

1. A dense star conjugate which comprises a dendrimer polymer complexed with a carried material, the carried material being salicylic acid and the dedrimer polymer comprising a polyamidoamine.

2. A formulation which comprises a conjugate of claim 1 having at least one pharmaceutically acceptable diluent or carrier present.

3. A pharmaceutically acceptable composition comprising salicylic acid complexed to a branched polyamidoamine carrier, and a diluent.

4. The composition of claim 3 wherein the carrier molecule is complexed to the salicylic acid by ionic, covalent, or Van der Waals bonding.

* * * * *